United States Patent
Mingozzi et al.

(10) Patent No.: US 10,640,785 B2
(45) Date of Patent: May 5, 2020

(54) VIRUS VECTORS FOR HIGHLY EFFICIENT TRANSGENE DELIVERY

(71) Applicant: THE CHILDREN'S HOSPITAL OF PHILADELPHIA, Philadelphia, PA (US)

(72) Inventors: Federico Mingozzi, Paris (FR); Xavier Anguela, Philadelphia, PA (US); J. Fraser Wright, Princeton, NJ (US); Katherine A. High, Merion Station, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 0 days.

(21) Appl. No.: 14/360,151

(22) PCT Filed: Nov. 21, 2012

(86) PCT No.: PCT/US2012/066380
§ 371 (c)(1),
(2) Date: May 22, 2014

(87) PCT Pub. No.: WO2013/078400
PCT Pub. Date: May 30, 2013

(65) Prior Publication Data
US 2014/0336245 A1  Nov. 13, 2014

Related U.S. Application Data

(60) Provisional application No. 61/682,019, filed on Aug. 10, 2012, provisional application No. 61/639,025, filed on Apr. 26, 2012, provisional application No. 61/562,795, filed on Nov. 22, 2011.

(51) Int. Cl.
*C12N 15/86* (2006.01)
*C12N 9/64* (2006.01)
*A61K 38/00* (2006.01)

(52) U.S. Cl.
CPC ............. *C12N 15/86* (2013.01); *C12N 9/644* (2013.01); *A61K 38/00* (2013.01); *C12N 2750/14123* (2013.01); *C12N 2750/14143* (2013.01)

(58) Field of Classification Search
None
See application file for complete search history.

(56) References Cited

U.S. PATENT DOCUMENTS

| | | |
|---|---|---|
| 2006/0258005 A1 | 11/2006 | Mayumi et al. |
| 2008/0044386 A1 | 2/2008 | Ji et al. |
| 2008/0220015 A1 | 9/2008 | Abina |
| 2009/0317417 A1 | 12/2009 | Vandenberghe et al. |
| 2010/0286242 A1 | 11/2010 | Bohn et al. |

FOREIGN PATENT DOCUMENTS

| | | |
|---|---|---|
| WO | 2000/032233 A2 | 6/2000 |
| WO | 2004027019 A2 | 4/2004 |
| WO | 2004/072289 A1 | 8/2004 |
| WO | 2005/118792 A1 | 12/2005 |
| WO | 2013/123503 A1 | 8/2013 |

OTHER PUBLICATIONS

Urabe, et al. (2006) "Removal of Empty Capsids from Type 1 Adeno-Associated Virus Vector Stocks by Anion-Exchange Chromatography Potentiates Transgene Expression", Molecular Therapy, 13(4): 823-28.*
Kay, et al. (2000) "Evidence for gene transfer and expression of factor IX in haemophilia B patients treated with an AAV vector", Nature Genetics, 24(3): 257-61.*
Mingozzi, F. et al., Overcoming Preexisting Humoral Immunity to AAV Using Capsid Decoys, Science Translational Medicine, 2013, 5(192-196):122-130.
Qu, G., et al., Separation of Adeno-Associated Virus Type 2 Empty Particles from Genome Containing Vectors by Anion-Exchange Column Chromatography, Journal of Virological Methods, 2007, 140:183-192.
Scallan et al., Human Immunoglobulin Inhibits Liver Transduction by AAV Vectors at Low AAV2 Neutralizing Titers in SCID Mice, Blood, 2005, 107:1810-1817.
International Search Report dated Mar. 19, 2013 of International Application No. PCT/US2012/066380.
Allay, J.A., et al., Good Manufacturing Practice Production of Self-Complementary Serotype 8 Adeno-Associated Viral Vector for a Hemophilia B Clinical Trial, Human Gene Therapy, 2011, 22:595-604.
Opie, S.R., et al., Identification of Amino Acid Residues in the Capsid Proteins of Adeno-Associated Virus Type 2 that Contribute to Heparan Sulfate Proteoglycan Binding, Journal of Virology, 2003, 77(12):6995-7006.

(Continued)

*Primary Examiner* — Robert M Kelly
(74) *Attorney, Agent, or Firm* — Robert M. Bedgood; Pillsbury Winthrop Shaw Pittman LLP

(57) ABSTRACT

The invention provides viral vector formulations and methods of uses thereof for delivery of transgenes or therapeutic nucleic acids to human subjects. The formulations include a vector and suitable amounts of empty capsids, viral genome-containing capsids, or viral capsid proteins which are optionally chemically or structurally modified and which bind to neutralizing anti-AAV antibodies thereby reducing or preventing antibody-mediated clearance of the vector, but still allowing the genome-containing (therapeutic) vector to transduce target cells and achieve therapeutic gene transfer.

28 Claims, 21 Drawing Sheets

Specification includes a Sequence Listing.

(56) References Cited

OTHER PUBLICATIONS

Golmohammadi, R., et al., The Crystal Structure of Bacteriophage QB at 3.5 Delta Resolution, Structure, 1996, 4(5):543-554.
Pien, G.C., et al., Capsid Antigen Presentation Flags Human Hepatocytes for Destruction After Transduction by Adeno-Associated Viral Vectors, The Journal of Clinical Investigation, 2009, 119(6):1688-1695.
Grimm, D., et al., Preclinical in vivo evaluation of pseudotyped adeno-associated virus vectors or liver gene therapy, Blood, 2003, 102(7):2412-2419.
Parker, A., et al., 1013. In Vivo Petiormance of AAV2 Vectors Purified by CsCl Gradient Centrifugation or Column Chromatography, Molecular Therapy, 2003, 7(5):S390-S391.
Sommer, J.M., et al., Quantification of Adeno-Associated Virus Particles and Empty Capsids by Optical Density Measurement, Molecular Therapy, 2003, 7(1):122-128.
Australian Patent Application No. 2012340567, Patent Examination Report No. 1, dated Nov. 11, 2016.
Australian Patent Application No. 2012340567, Patent Examination Report No. 2, dated Oct. 31, 2017.
European Patent Application No. 12851878.4, Supplementary European Search Report, dated Jun. 26, 2015.
European Patent Application No. 12851878.4, Communication Pursuant to Article 94(3) EPC and Annex to Communication, dated Jul. 27, 2016.
European Patent Application No. 12851878.4, Further Communication Pursuant to Article 94(3) EPC and Annex to Communication, dated Jul. 6, 2017.
European Patent Application No. 12851878.4, Summons to attend oral proceedings pursuant to Rule 115(1) EPC and Annex to Communication, dated Jun. 27, 2018.
Croyle, M.A., et al., Development of formulations that enhance physical stability of viral vectors for gene therapy, Gene Therapy, 2001, 8:1281-1290.
Maersch, S., et al., Optimization of stealth adeno-associated virus vectors by randonization of immunogenic epitopes, Virology, 2010, 397:167-175.

\* cited by examiner

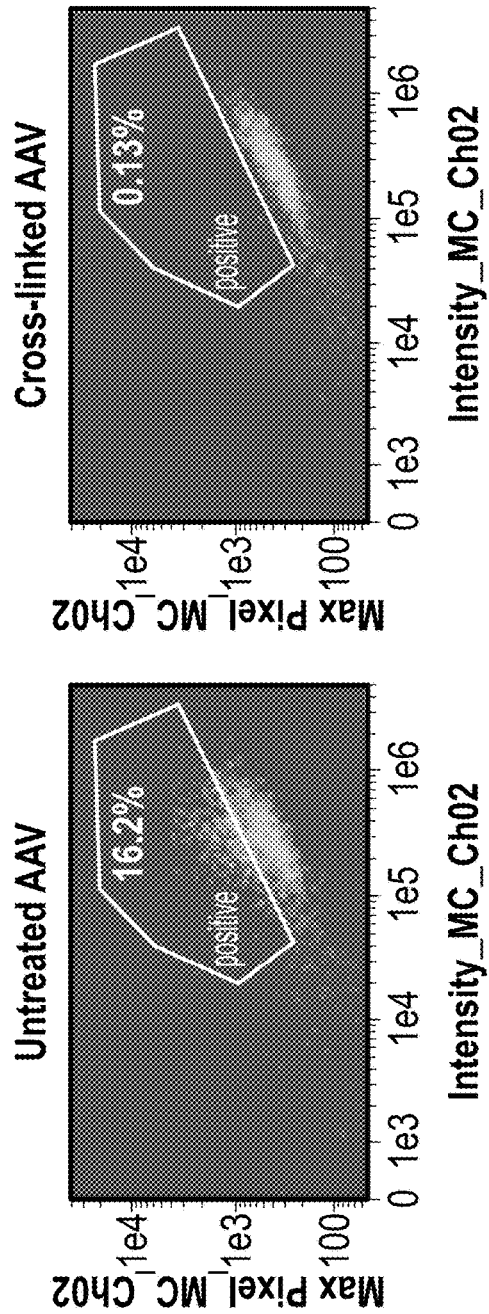
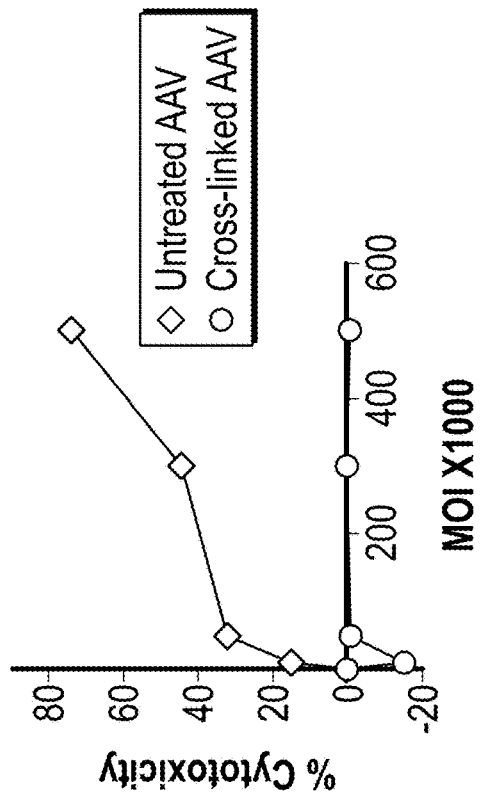
Figure 4A
Figure 4B

Figure 10
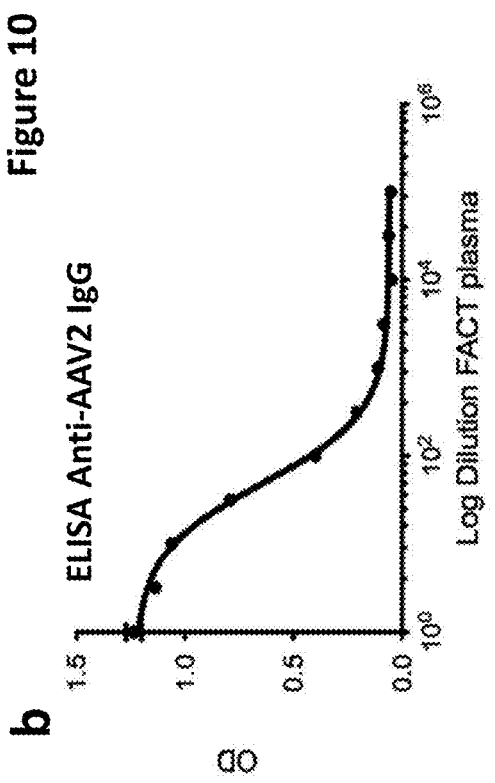
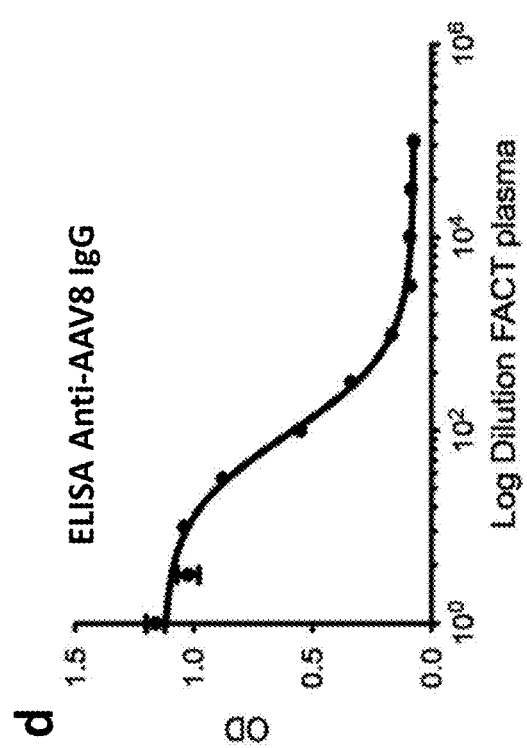
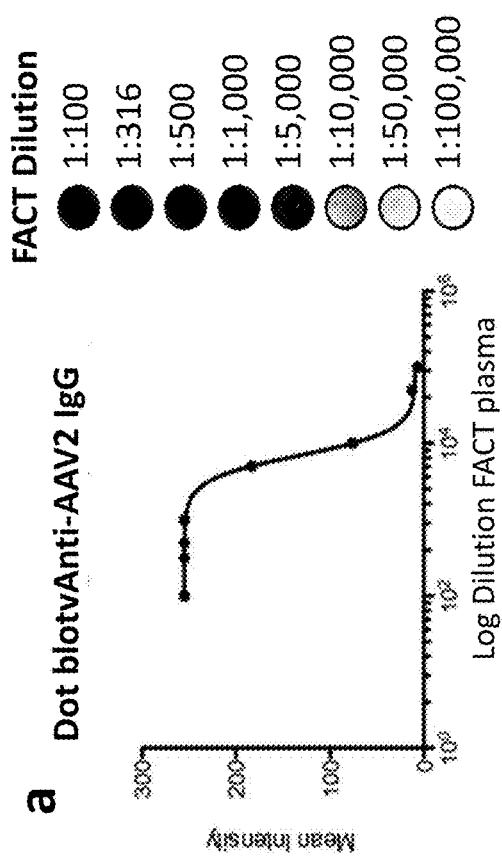
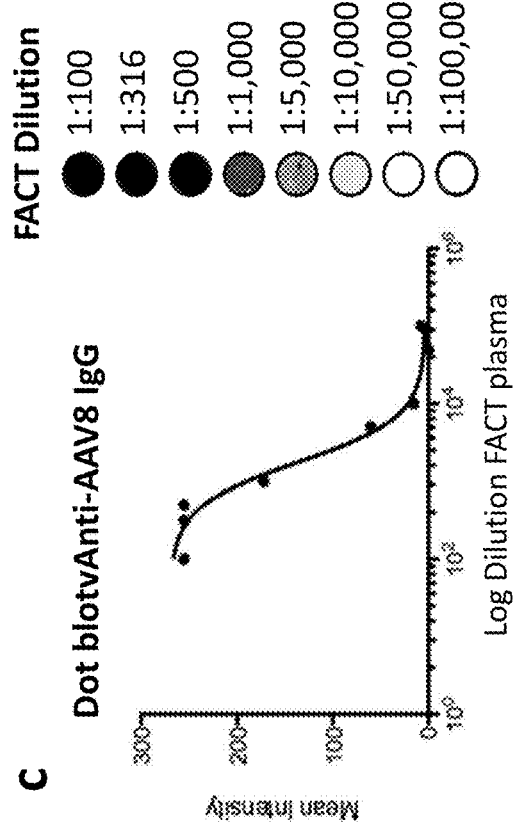

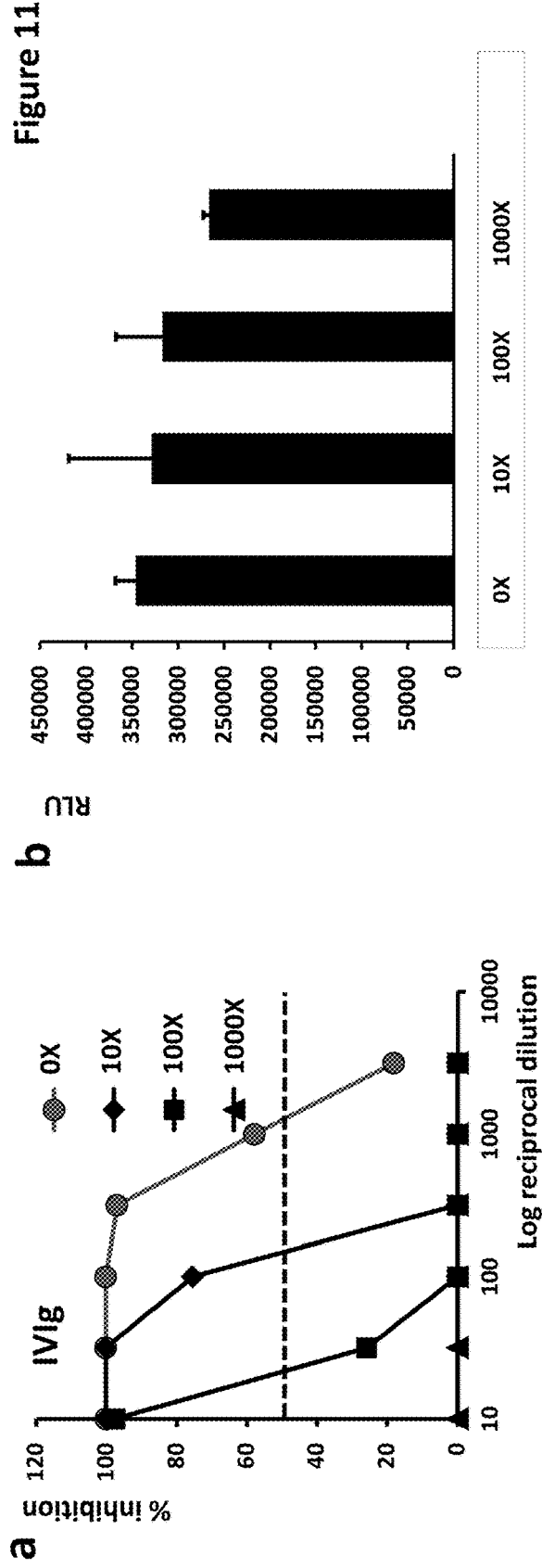
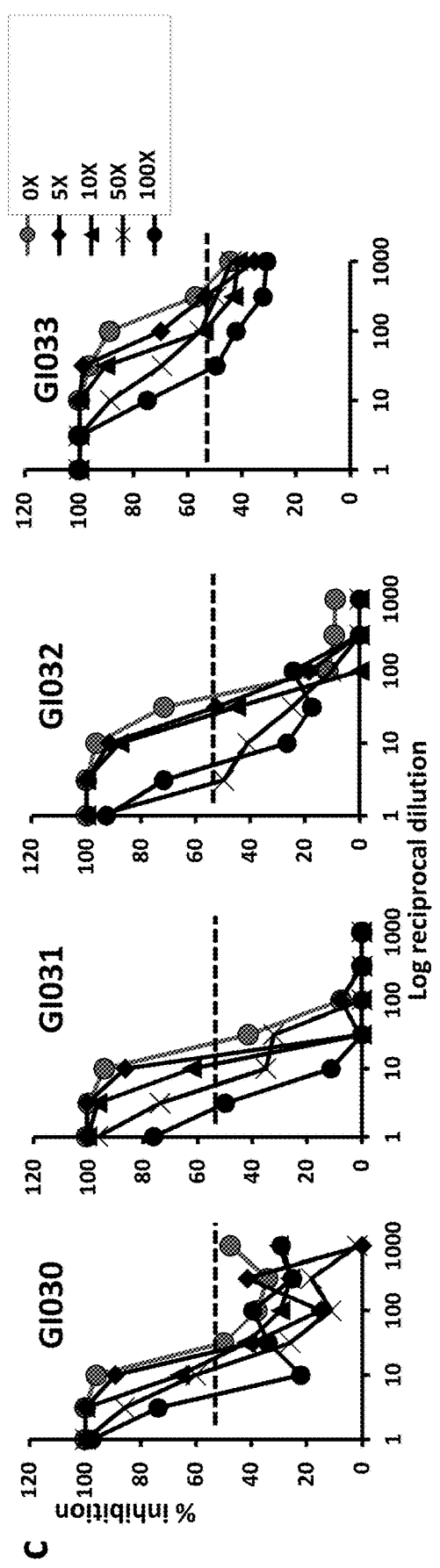
Figure 11

Figure 16

| Subj. ID | One year-old subjects ||||  Subj. ID | Adult subjects ||||
| | Neutralizing antibodies || Total antibodies || | Neutralizing antibodies || Total antibodies ||
| | NAb titer | % inhibition undiluted serum | Dot Blot | Integrated intensity* | | NAb titer | % inhibition undiluted serum | Dot Blot | Integrated intensity* |
|---|---|---|---|---|---|---|---|---|---|
| Ped1 | 1 | 46 | ○ | 2 | GI049 | 1 | 50 | ● | 100 |
| Ped2 | 1 | 10 | ○ | 4 | GI058 | 1 | 48 | ◐ | 15 |
| Ped3 | 1 | 20 | ○ | 7 | GI070 | 1 | 14 | ○ | 12 |
| Ped4 | 1 | 0 | ○ | 0 | GI080 | 1 | 20 | ◐ | 23 |
| Ped5 | 1 | 11 | ○ | 0 | GI082 | 1 | 25 | ○ | 9 |
| Ped6 | 1 | 8 | ○ | 0 | GI095 | 1 | 0 | ○ | 3 |
| Ped7 | 1 | 10 | ○ | 1 | GI099 | 1 | 41 | ◐ | 15 |
| Ped8 | 1 | 0 | ○ | 0 | GI102 | 1 | 22 | ○ | 6 |
| Ped9 | 1 | 20 | ○ | 0 | GI105 | 1 | 0 | ○ | 16 |
| Ped10 | 1 | 0 | ○ | 0 | GI133 | 1 | 27 | ○ | 9 |

Figure 17

| Animal ID | Vector dose (vg/kg) | Empty capsids (cp/kg) | Neutralizing Ab | | Total Ab | | Week 6 hFIX levels (ng/ml) |
|---|---|---|---|---|---|---|---|
| | | | Anti-AAV8 NAb titer* | % inhibition undiluted serum | Dot Blot | Integrated intensity*,# | |
| 1001 | $1 \times 10^{12}$ | - | 1 | 50 | ● | 79 | $0^{\S}$ |
| 1002 | $1 \times 10^{12}$ | - | 1 | 34 | ○ | 41 | 67 |
| 2001 | $1 \times 10^{12}$ | $9 \times 10^{12}$ | 1 | 32 | ○ | 18 | 347 |
| 3001 | $2 \times 10^{12}$ | - | 1 | 57 | ● | 100 | 0 |
| 3002 | $2 \times 10^{12}$ | - | 1 | 10 | ● | 85 | 169 |
| 4001 | $2 \times 10^{12}$ | $1.8 \times 10^{13}$ | 1 | 80 | ○ | 36 | 415 |
| 4002 | $2 \times 10^{12}$ | $1.8 \times 10^{13}$ | 1 | 55 | ○ | 40 | 915 |

Figure 18

| Tissue | Animal ID: 3001 | | Animal ID: 3002 | | Animal ID: 4001 | | Animal ID: 4002 | |
|---|---|---|---|---|---|---|---|---|
| | Avg | StDev | Avg | StDev | Avg | StDev | Avg | StDev |
| Liver caudate lobe 1 | 0.0007 | 0.0001 | 0.3014 | 0.0145 | 0.0206 | 0.0173 | 0.5677 | 0.0339 |
| Liver caudate lobe 2 | 0.0065 | 0.0030 | 0.1333 | 0.0199 | 0.0011 | 0.0007 | 0.4514 | 0.0312 |
| Liver left lateral lobe 1 | 0.0112 | 0.0057 | 0.1990 | 0.0338 | 0.0713 | 0.0286 | 0.0163 | 0.0079 |
| Liver left lateral lobe 2 | 0.0056 | 0.0042 | 0.1086 | 0.0112 | 0.0454 | 0.0121 | 0.6604 | 0.0196 |
| Liver right lateral lobe 1 | 0.0379 | 0.0054 | 0.1934 | 0.0065 | 0.0506 | 0.0105 | 0.5458 | 0.0160 |
| Liver right lateral lobe 2 | 0.0047 | 0.0031 | 0.0087 | 0.0028 | 0.0599 | 0.0292 | 0.3821 | 0.0378 |
| Liver left medial lobe 1 | 0.0049 | 0.0025 | 0.0128 | 0.0051 | 0.2285 | 0.0198 | 0.5091 | 0.0436 |
| Liver left medial lobe 2 | 0.0057 | 0.0040 | 0.1437 | 0.0128 | 0.1451 | 0.0186 | 0.0109 | 0.0035 |
| Liver right medial lobe 1 | 0.0018 | 0.0004 | 0.0341 | 0.0128 | 0.1202 | 0.0129 | 0.6715 | 0.0373 |
| Liver right medial lobe 2 | 0.0077 | 0.0056 | 0.0056 | 0.0022 | 0.0128 | 0.0012 | 0.6134 | 0.0210 |
| Liver quadrate lobe 1 | 0.0051 | 0.0018 | 0.0160 | 0.0047 | 0.1629 | 0.0215 | 0.7107 | 0.0377 |
| Liver quadrate lobe 2 | 0.0030 | 0.0013 | 0.0294 | 0.0086 | 0.0170 | 0.0069 | 0.0130 | 0.0054 |
| Average Liver | 0.0079 | 0.0098 | 0.0988 | 0.0969 | 0.0780 | 0.0710 | 0.4294 | 0.2673 |
| Brain | 0.0093 | 0.0048 | 0.0254 | 0.0233 | 0.0173 | 0.0124 | 0.0377 | 0.0063 |
| Kidney | 0.0265 | 0.0175 | 0.0959 | 0.0624 | 0.0115 | 0.0038 | 0.0091 | 0.0016 |
| Spleen | 0.0322 | 0.0203 | 0.0273 | 0.0092 | 0.0099 | 0.0060 | 0.0310 | 0.0196 |
| Thymus | 0.0136 | 0.0056 | 0.0000 | 0.0000 | 0.0000 | 0.0000 | 0.0333 | 0.0076 |
| Testes | 0.0155 | 0.0086 | 0.1030 | 0.1204 | 0.0259 | 0.0073 | 0.0079 | 0.0015 |
| Lung | 0.0388 | 0.0175 | 0.0013 | 0.0011 | 0.0790 | 0.0580 | 0.1120 | 0.0380 |
| Diaphragm | 0.1995 | 0.1130 | 0.1194 | 0.0771 | 0.1267 | 0.0354 | 0.1458 | 0.0816 |
| Psoas | 0.0919 | 0.0239 | 0.2118 | 0.0549 | 0.0812 | 0.0143 | 0.1199 | 0.0405 |
| Heart | 0.0083 | 0.0058 | 0.0740 | 0.0478 | 0.0150 | 0.0164 | 0.0347 | 0.0177 |

VIRUS VECTORS FOR HIGHLY EFFICIENT TRANSGENE DELIVERY

RELATED APPLICATIONS

This application is the National Phase of International Application No. PCT/US2012/066380, filed Nov. 21, 2012, which designated the U.S. and that International Application was published under PCT Article 21(2) in English, which claims priority to Application Ser. No. 61/682,019, filed Aug. 10, 2012, Application Ser. No. 61/639,025, filed Apr. 26, 2012, and Application Ser. No. 61/562,795, filed Nov. 22, 2011, all of which applications are expressly incorporated herein by reference in their entirety.

GOVERNMENT SUPPORT

This invention was made with government support under Grant No. HL078810 awarded by the National Institutes of Health and the Howard Hughes Medical Institute. The U.S. Government has rights in the invention.

FIELD OF THE INVENTION

This application relates to the fields of gene therapy and molecular biology. More specifically, this invention provides compositions of adeno-associated viral vectors which have been formulated to mitigate virus neutralization and avoid undesirable anti-AAV immune responses thus providing for efficient intravascular delivery and more predictable expression of therapeutic polynucleotides and the capacity for re-administration in the presence of existing anti-vector immunity.

INTRODUCTION

Adeno-associated virus is a helper-dependent virus of the family parvoviridae, subfamily parvovirinae, genus *dependovirus*, species *adeno*-associated virus. It requires a helper virus for replication, so natural infections take place in the context of infection with a helper virus such as adenovirus. Infection with adeno-associated virus causes no known pathologies. Adeno-associated virus (AAV) vectors are scalable, efficient, non-cytopathic gene delivery vehicles used primarily for the treatment of genetic diseases (Mingozzi F., et al., *Nat. Rev. Genet.* 2011; 12:341-355). Their ability to transduce non-dividing cells and persist episomally results in long-term transgene expression in animals A. broad spectrum of animal models of human diseases has been successfully treated by AAV vectors, including diseases of the brain, heart, lung, eye and liver (Mingozzi F., et al., *Nat. Rev. Genet.* 2011; 12:341-355). Hemophilia B is an approachable target for the use of gene transfer vectors because therapeutic benefits can be realized through expression of as little as 1-2% of wild-type levels of Factor IX (hFIX) (High K A., *Ann. NY Acad. Sci.* 2001; 953:64-74).

Adeno-associated virus (AAV) vectors are among the most promising viral vectors for in vivo gene transfer. In recent years several studies in experimental animal models and in humans showed the potential of this therapeutic platform. In particular, convincing efficacy data have been obtained in humans affected by RPE65 deficiency and by hemophilia B. Several AAV-based gene transfer products are now in clinical testing for a number of indications, and in some cases clinical development is approaching late-phase and licensing.

Despite the promise of AAV based gene therapy approaches for treatment of a variety of disorders, immune responses occur following exposure to adeno-associated virus (AAV) or AAV vectors, and these protective responses may limit therapeutic efficacy of AAV vectors. Humoral responses (anti-AAV neutralizing antibodies, or NAb) often give rise to viral neutralization causing a significant reduction in viral transduction of the target cell, thereby limiting the amount of therapeutic polypeptide delivered. Anti-AAV neutralizing antibodies can efficiently neutralize AAV vectors; this has been reported in humans (Manno C. S., et al., *Nat Med.* 2006; 12:342-347), mice (Scallan C. D., et al., *Blood.* 2006; 107:1810-1817), and non-human primates (Jiang H., et al., *Blood.* 2006; 108:3321-3328). Subjects exposed to AAV vectors showed humoral immune responses, including IgM and IgG responses to AAV capsid of all four IgG subclasses. IgG responses to AAV capsid in clinical trial subjects were inversely proportional to the level of pre-existing anti-AAV antibody and independent of the vector dose. Humans are also naturally exposed to wild type AAV, thus they develop antibodies that cross react with all AAV serotypes. An additional complication is that the assays currently in place to screen for NAb are not very sensitive, and therefore even subjects who test negative or low titer on these assays may in fact have low levels of anti-AAV antibodies are sufficient to block AAV transduction.

In addition to antibody responses, individuals exposed to AAV vectors also develop cytotoxic T cell (CTL) responses directed specifically against the AAV vector capsid (Li H., et al., *Nature.* 475, 217-221 (2011); Arruda V. R., et al., *Blood.* 115, 4678-4688 (2010); Chen Y. H., et al., *Nat. Med.* 15, 1215-1218 (2009); Boutin S., et al., *Hum. Gene. Ther.* 21, 704-712 (2010); Calcedo R., et al., *J. Infect. Dis.* 199, 381-390 (2009)). These CTL responses are responsible for the clearance of AAV vector transduced cells with consequent limited therapeutic efficacy. CTL responses are triggered in a vector dose-dependent manner (Li H., et al., *Nature.* 475, 217-221 (2011); Chen Y. H., et al., *Nat. Med.* 15, 1215-1218 (2009); Calcedo R., et al., *J. Infect. Dis.* 199, 381-390 (2009)), thus underlying the importance of achieving high levels of transduction efficiency at lower vector doses.

The difficulty for the gene therapist is that the obvious solution to the first obstacle, using higher titers of vector to increase cell transduction, tends to encroach on successful avoidance of the second, which requires that the overall vector dose be as low as possible to avoid eliciting anti-vector responses and destruction of transduced cells. Accordingly, improved formulations of AAV vectors which ameliorate or avoid the aforementioned drawbacks are highly desirable.

SUMMARY

In accordance with the invention, viral vector formulations for administration and gene transduction by way of gene therapy are provided. In one embodiment, a formulation comprises a predetermined ratio of viral vectors and empty capsids, wherein the viral vector includes a transgene and the predetermined amount of empty capsids is calculated to inhibit undesired immune responses to said formulation in said patient. In another embodiment, a formulation comprises a predetermined ratio of viral vectors and viral genome containing capsids wherein the viral vector includes a transgene and the predetermined amount of viral genome containing capsids is calculated to inhibit undesired immune responses to said formulation in said patient. In still another embodiment, a formulation comprises a predetermined ratio of viral vectors and capsid proteins wherein the viral vector includes a transgene and the predetermined amount of capsid proteins is calculated to inhibit undesired immune responses to said formulation in said patient.

In accordance with the invention, also provided are methods of increasing or improving gene transduction by way of gene therapy to a patient are provided by employing a viral vector formulation. In one embodiment, a method includes administering a viral vector comprising a transgene to a cell; and administering empty capsids, viral genome-containing capsids, or viral capsid proteins to the subject in an amount effective to increase or improve transduction of a transgene into the cell. In another embodiment, a method includes administration of a predetermined ratio of viral vectors and administration of empty capsids, wherein the viral vector includes a transgene and the predetermined amount of empty capsids is calculated to inhibit undesired immune responses to said formulation in said patient. In a further embodiment, a method includes administration of a predetermined ratio of viral vectors and viral genome containing capsids wherein the viral vector includes a transgene and the predetermined amount of viral genome containing capsids is calculated to inhibit undesired immune responses to said formulation in said patient. In still another embodiment, a method includes administration of a predetermined ratio of viral vectors and capsid proteins wherein the viral vector includes a transgene and the predetermined amount of capsid proteins is calculated to inhibit undesired immune responses to said formulation in said patient.

In accordance with the invention, further provided are methods for reducing or inhibiting an immune response against a viral vector that includes a transgene. In one embodiment, a method includes administering a viral vector that includes the transgene to a subject; and administering empty capsids, viral genome-containing capsids, or viral capsid proteins to the subject in an amount effective to reduce or inhibit an immune response against the viral vector that includes the transgene.

In such methods, the viral vectors and empty capsids can be administered separately (e.g., sequentially), the viral vectors and viral genome containing capsids can be administered separately (e.g., sequentially), and the viral vectors and capsid proteins can be administered separately (e.g., sequentially). In such methods, viral vectors and empty capsids can be administered concomitantly or as a combination, the viral vectors and viral genome containing capsids can be administered concomitantly or as a combination, and the viral vectors and capsid proteins can be administered concomitantly or as a combination.

In particular embodiments of invention formulations, compositions, methods and uses disclosed herein, the viral vectors and capsids (empty or genome containing) or capsid proteins are adeno-associated virus (AAV) vectors or AAV capsids. Such AAV vectors, capsids (empty or genome containing) or capsid proteins can be identical or different serotypes, and can be any naturally and non-naturally occurring AAV serotypes. Such non-limiting serotypes include, for example, AAV-1, -2, -3, -4, -5, -6, -7, -8, -9, -10, -11, -rh74, -rh10 and AAV-2i8.

In one aspect, empty capsids, viral genome containing capsids or capsid proteins are unmodified. In another aspect, empty capsids, viral genome containing capsids or capsid proteins are modified to reduce or inhibit cellular uptake. In a particular aspect, capsids, viral genome containing capsids or capsid proteins can be cross-linked (e.g., chemically), or modified (amino acid residues substituted to reduce receptor binding). In further particular aspects, viral envelope (e.g., capsids) are modified (e.g., mutated) to reduce binding to a cell receptor (e.g., binding to heparan sulfate proteoglycan). In various such aspects, unmodified or modified proteins (e.g., capsid protein) of the empty capsid, viral genome containing capsids or capsid proteins has a reduced ability to bind to receptor (e.g., bind to heparan sulfate proteoglycan) or to transduce cells (in vitro, ex vivo or in vivo), as compared to the viral vectors which contain the transgene. In other such aspects, viral vectors which contain the transgene has a greater ability to bind to receptor (e.g., bind to heparan sulfate proteoglycan) or to transduce cells (in vitro, ex vivo or in vivo), as compared to the unmodified or modified proteins (e.g., capsid protein) of the empty capsid, viral genome containing capsids or capsid proteins.

In additional aspects, the vectors and capsids (empty or genome containing) or capsid proteins are present in a biologically acceptable carrier suitable for administration. In various aspects, systemic, regional or local administration of the formulation is employed.

Also provided is a method for delivering a transgene to a cell which comprises administration of an effective amount of the formulation to a patient in need thereof. In one embodiment, the patient has a metabolic or genetic disorder and the transgene encodes a therapeutic molecule which corrects or ameliorates one or more symptoms of the disorder.

Any serotype of AAV may be employed in the formulations and methods and uses of the invention. In one approach, the capsids (empty or genome containing) or capsid proteins and viral vectors are from the same serotype. In another approach, the capsids (empty or genome containing) or capsid proteins and viral vectors are obtained from different serotypes of AAV.

DESCRIPTION OF DRAWINGS

FIGS. 4A-4D show data indicating that cross-linking of AAV vectors results in impaired cell entry and reduced binding and uptake by human dendritic cells. (a) Untreated and cross-linked AAV vector internalization in HHL5 human hepatocytes. Cells were treated for 1 hr at an MOI of $1\times10^5$ with AAV2 vectors and subsequently intracellularly stained with the anti-AAV2 monoclonal antibody A20. The gate and the % indicate the amount of AAV signal localized intracellularly. (b) CTL assay with HHL5 human hepatocytes. Target cells were transduced overnight at increasing MOIs of untreated or cross-linked AAV vectors and incubated with AAV-specific effector cells at an effector:target ratio of 10:1. % cytotoxicity is calculated after background subtraction relative to the max cell lysis obtained by treating targets with TritonX. (c,d) Human monocyte-derived DCs were transduced with untreated or cross-linked AAV2 vectors at an MOI of $1\times10^5$ and then intracellularly stained with the anti-AAV2 antibody A20 and DRAQ5 (c) or an anti-CD71 antibody (d). (c) Vector internalization. Upper panels, vector is shown in green, nuclear stain in red. For both vectors one representative cell of at least 5000 collected is shown. CH1, bright field; CH2 vector; CH5 nucleus; CH2/5 overlay. The histogram plots show the percent of internalized AAV after 1 hour (top panels) and 4 hours (bottom panels) for untreated and cross-linked AAV. (d) Colocalization of the vector in early endosomes 4 hours after transduction. Upper panels, vector is shown in green, endosome stain in purple. For both vectors one representative cell of at least 5000 collected is shown. CH1, bright field; CH2 vector; CH3 endosome; CH2/3 overlay. Dot plots: the gates and the percent values indicate the cells double positive for endosomal staining and vector staining. Histograms: the gates and the percent values indicate the cells gated in the dot plots in which the staining for vector and endosomes is colocalized.

FIGS. 10A-10D show a comparison of the dot blot assay with an ELISA assay for the detection of anti-AAV IgG. In both assays, anti-IgG heavy and light chain antibodies were used. For the ELISA, wells were coated with 1 mg/ml of AAV capsid overnight in coating buffer. After blocking, serial dilutions of FACT plasma were added to each well and incubated overnight at 4° C. Detection of bound IgG was done with an HRP-conjugated antibody used at a dilution of 1:1,000. (a,c) Dot blot assay for the detection of anti-AAV2 (a) and -AAV8 (c) IgG. Plots represent the mean intensities measured by densitometry; a representative picture of the dot blot at each FACT dilution is also shown. (b, d) Anti-AAV2 (b) and -AAV8 (d) antibody ELISA assay. Plots represent the optical densities (OD) at each given FACT dilution.

FIGS. 11A-11C show data indicating that AAV empty capsids prevent vector neutralization by anti-AAV NAb but, only when in vast excess, do not inhibit transduction in vitro. (a) An AAV8 vector expressing luciferase (AAV8-Luciferase, MOI $1 \times 10^3$) alone (green line), or in the presence of excess empty AAV8 capsids (10×, 100×, or 1000× the MOI), was incubated with ½ log dilutions of IVIg. % inhibition was determined compared to intensity of the reporter signal for AAV8-Luciferase vector not incubated with IVIg. (b) Effect of empty capsids on efficiency of transduction in vitro of an AAV vector expressing luciferase. MOI $1 \times 10^3$; amount of excess empty capsids is indicated in the x-axis as fold over the MOI. RLU, relative light units. (c) Effect of addition of an excess (5×, 10×, 50×, 100×) of empty AAV8 capsid on the neutralizing activity of serum from human subjects with hemophilia B; the assay was performed as described for IVIg in panel A.

FIG. 16 shows a table of the prevalence of anti-AAV8 antibodies in children and adults (representative set), *% of max (mean integrated density after background subtraction).

FIG. 17 shows a dot blot assay table summarizing the findings of varying amounts of anti-AAV8 IgG in non-human primates. Ab, antibodies; *Baseline values; #% of max (mean integrated density after background subtraction).

FIG. 18 shows AAV8-FIX vector biodistribution in non-human primates. Each animal received $2 \times 10^{12}$ vg/kg of vector. Animals 4001 and 4002 received a vector formulated in 9× empty capsids. Results are reported as vector genomes copy number per diploid genome. Avg, average of triplicate testing. StDev, standard deviation.

DETAILED DESCRIPTION

Figure 1:
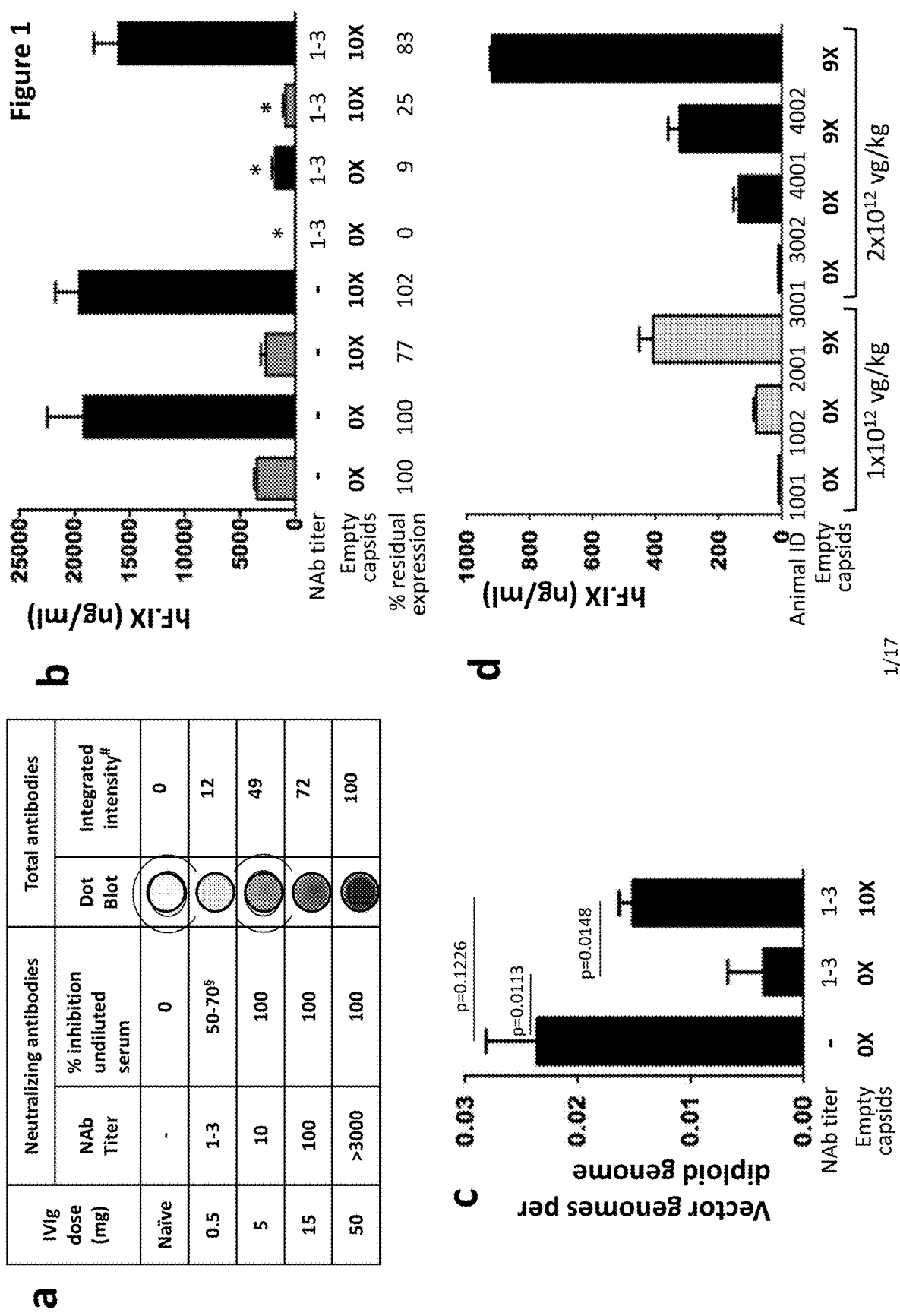
FIGS. 1A-1D show data indicating that AAV empty capsids prevent vector neutralization by anti-AAV NAb in vivo in mice and in non-human primates. (a) Anti-AAV8 antibody analysis in naïve mice injected intraperitoneally (IP) with PBS only, or mice passively immunized IP with 0.5 mg, 5 mg, 15 mg, or 50 mg of IVIg (n=5 per group). The analysis was performed 24 hours after immunization. Neutralizing antibody (Nab) titer represents the reciprocal serum dilution at which <50% inhibition of the reporter vector signal was measured in the NAb assay. Integrated intensity represents the average pixel intensity in the dot blot assay after background subtraction; §, range; #, percent of max signal intensity. (b) Male C57BL/6 mice (n=5 per group) were immunized with 0.5 mg of IVIg (resulting in a NAb titer of 1-3) or injected with PBS (−). After 24 hours, animals received either $1\times10^9$ vg (grey bars) or $5\times10^9$ vg (black bars) of an AAV8-F.IX vector alone (0×) or formulated with a 10× excess of AAV8 empty capsids ($1\times10^{10}$ cp (grey bars) or $5\times10^{10}$ cp (black bars)). Human F.IX transgene levels in plasma at week 8 post vector delivery are shown as average; error bars, standard deviation of the mean. The % residual expression is calculated relative to the F.IX transgene plasma levels in naïve animals receiving the AAV-F.IX vector. *, $p<0.05$ vs. naïve mice. (c) Vector gene copy number in mouse livers collected at week 12 after AAV8-F.IX gene transfer at a vector dose of $5\times10^9$ vg per animal Results are shown as average copy number of 5 livers. Error bars, standard deviation of the mean. Experimental groups are the same as shown in panel b. (d) Plasma human F.IX levels in male rhesus macaques receiving an AAV8-hF.IX vector at doses of $1\times10^{12}$ vg/kg (grey bars) or $2\times10^{12}$ vg/kg (black bars) Animals received the AAV8-hF.IX vector in PBS (0×), or formulated in excess of empty AAV8 capsids (9×). Results are shown as average of hF.IX levels in plasma at weeks 4 to 8 (weekly measurements). Error bars, the standard deviation of the mean.

The invention disclosed herein involves formulations, methods and uses of AAV empty capsids (inactive AAV that do not carry a genome and/or that can be modified or cross-linked so that they are unable to enter a cell) or genome (e.g., viral) containing capsids in a formulation of AAV vectors (active AAV vectors carrying a transgene).

AAV empty or genome (viral) containing capsids used in this manner act as vector decoys that are bound by neutralizing antibodies (NAbs) and thus prevent them from neutralizing AAV vectors (containing a transgene), resulting in superior gene transduction efficiency when AAV vectors are delivered to a cell, e.g., through the bloodstream.

As used herein, "gene therapy" is the insertion of nucleic acid sequences (e.g., genes) into an individual's cells and/or tissues to treat a disease, commonly hereditary diseases wherein a defective mutant allele is replaced or supplemented with a functional one. Acquired diseases such as blood clotting disorders, congestive heart failure are amenable to gene therapy. Gene therapy also includes insertion of nucleic acids that are inhibitory in nature, i.e., polynucleotides that inhibit, decrease or reduce expression, activity or function of an endogenous gene or protein, such as an undesirable or aberrant (e.g., pathogenic) gene or protein.

"Adeno-associated viruses" (AAV), from the parvovirus family, are small viruses with a genome of single stranded DNA. These viruses are useful as gene therapy vectors as they can penetrate cells and introduce nucleic acid/genetic material, for example, at a specific site on chromosome 19. Because AAV are not associated with pathogenic disease in humans, AAV vectors are able to deliver therapeutic proteins and agents to human patients without causing substantial AAV pathogenesis.

An "AAV vector" or simply "vector" is derived from the wild type AAV by using molecular methods to remove the wild type AAV genome, and replacing with a non-native nucleic acid, such as a therapeutic gene expression cassette. Typically, the inverted terminal repeats of the wild type AAV genome are retained in the AAV vector. An AAV vector is distinguished from an AAV, since all or a part of the viral genome has been replaced with a transgene, which is a non-native nucleic acid with respect to the AAV nucleic acid sequence.

"Empty viruses" or "empty capsids" as used herein do not contain a genome (hence, the term "empty"). By contrast, "genome (e.g., viral) containing capsids" contain a genome, typically a viral genome (e.g., AAV viral genome). Empty capsids are virus-like particles in that they react with one or more antibodies that reacts with the intact (genome containing viral vector) virus (e.g. adeno-associated virus, AAV). For example, an empty AAV8 capsid would retain the ability to react with one or more antibodies that bind to an AAV,
such as an AAV8 or an AAV8 vector, or another AAV serotype. For example, an empty AAV2 capsid would retain the ability to react with one or more antibodies that bind to AAV8 or an AAV8 vector.

Empty (or genome containing) capsids may retain the ability to enter a cell, but are not required to enter a cell, for example, modifying or cross-linking a capsid protein sequence of empty (or genome containing) capsids reduces the ability of the modified or cross-linked capsids to enter cells. Thus, such empty capsids, genome containing capsids and capsid proteins may have reduced binding to a cell as compared to a viral vector that includes the transgene. Accordingly, empty capsids, genome containing capsids and capsid proteins may be unmodified, or modified, and have reduced binding to a cell as compared to a viral vector that includes the transgene. In particular embodiments, empty capsids, viral genome-containing capsids, or viral capsid proteins are treated with a cross-linking agent, or comprise mutated capsids that exhibit reduced or decreased binding to AAV receptor. In particular aspects, a mutated capsid comprises one or more arginine (R) residues that contribute to heparan sulfate proteoglycan binding that has been substituted with a non-charged or hydrophobic residue, or any AAV, such as AAV2, with one or more arginine (R) residues substituted at any of the following positions: 451, 448, 530, 585 or 588 (e.g., one or more arginine (R) residues substituted at any of position: 451 with a cysteine, 448 with a cysteine, 530 with an alanine, 585 with an alanine or 588 with an alanine). A representative AAV (AAV2) capsid sequence which illustrates representative positions (451, 448, 530, 585 and 588) that may be substituted, without and with R substitutions shown at positions 585 and 588, is as follows:

```
maadgylpdwledtlsegirqwwklkpgppppkpaerhkddsrglvlpgykylgpfngldkgepvnea daaalehdkaydrqldsgdnpylkynhadaefgerlkedtsfggnlgravfqakkrvleplglveepv ktapgkkrpvehspvepdsssgtgkagqqparkrinfgqtgdadsvpdpqplgqppaapsglgtntma tgsgapmadnnegadgvgnssgnwhcdstwmgdrvittstrtwalptynnhlykqissqsgasndnhy fgystpwgyfdfnrfhchfsprdwqrlinnnwgfrpkrinfklfniqvkevtqndgtttiannitstv qvftdseyqlpyvlgsahqgclppfpadvfmvpqygyltlnngsgavgrssfycleyfpsqmlrtgnn ftfsytfedvpfhssyahsqsldrlmnplidqylyylsrṭntp̣sgtttqsrlqfsgagasdirdqsrn wlpgpcyrqqrvsktsadnnnseyswtgatkyhlngrdslvnpgpamashkddẹekffpqsgvlifgk qgsektnvdiekvmitdeeeirttnpvateqygsystnlqRgnRqaatadvntqgvlpgmvwqdrdvy lqgpiwakiphtdghfhpsplmggfglkhpppgiliknptpvpanpsttfsaakfasfitqystgqvsv eiewelqkenskrwnpeiqytsnynksvnvdftvdtngvyseprpigtryltrnl.
```

Empty-AAV or empty capsids are sometimes naturally found in AAV vector preparations. Such natural mixtures can be used in accordance with the invention, or if desired be manipulated to increase or decrease the amount of empty capsid and/or vector. For example, the amount of empty capsid can be adjusted to an amount that would be expected to reduce the inhibitory effect that antibodies that react with an AAV vector that is intended to be used for vector-mediated gene transduction in the subject.

Empty capsids can also be produced independent of AAV vector preparations, and if desired added to AAV vector preparations, or administered separately to a subject. Empty capsids, genome containing capsids and capsid proteins can be generated and purified at a quality and their quantities determined, optionally adjusted, for example, according to=AAV antibody titer or serotype in the subject, and used or administered according to their intended purpose.

Empty capsids, genome containing capsids and capsid proteins are believed to bind to or react with antibodies against the viral vectors, thereby functioning as a decoy to reduce immune response against the viral vector. Such a decoy acts to absorb the antibodies directed against the viral vector thereby increasing or improving viral vector transgene transduction of cells (introduction of the transgene) in the context of such antibodies, and in turn increased cellular expression of the gene transcript and/or encoded protein.

The term "bind," "binding," or "react with" means that the antibody or empty capsid, genome containing capsid or capsid protein interacts at the molecular level. Thus, an empty capsid, genome containing capsid or capsid protein that binds to or reacts with an antibody interacts with the antibody at the molecular level.

As disclosed herein, empty capsids, genome containing capsids and capsid proteins of different serotypes are cross-reactive with antibodies against a particular serotype. Thus, for example an antibody against a given AAV serotype, such as AAV2, may also bind to one or more other AAV serotypes. Accordingly, a given AAV serotype, such as an AAV2 empty capsid, genome (e.g., viral) containing capsid or capsid protein can be used in a formulation or method or use of the invention in a combination with a different naturally or non-naturally occurring AAV serotype, such as AAV-1, -3, -4, -5, -6, -7, -8, -9, -10, -11, -rh74, -rh10 or AAV-2i8. Likewise, an AAV8 empty capsid, genome (e.g., viral) containing capsid or capsid protein can be used in a formulation or method or use of the invention in a combination with a different naturally or non-naturally occurring AAV serotype, such as AAV-1, 2, -3, -4, -5, -6, -7, -9, -10, -11, -rh74, -rh10 or AAV-2i8.

A "serotype" is traditionally defined on the basis of a lack of cross-reactivity between antibodies to one virus as compared to another virus. Such cross-reactivity differences are usually due to differences in capsid protein sequences/antigenic determinants (e.g., due to VP1, VP2, and/or VP3 sequence differences of AAV serotypes). Under the traditional definition, a serotype means that the virus of interest has been tested against serum specific for all existing and characterized serotypes for neutralizing activity and no antibodies have been found that neutralize the virus of interest. As more naturally occurring virus isolates of are discovered and capsid mutants generated, there may or may not be serological differences with any of the currently existing serotypes. Thus, in cases where the new AAV has no serological difference, this new AAV would be a subgroup or variant of the corresponding serotype. In many cases, serology testing for neutralizing activity has yet to be performed on mutant viruses with capsid sequence modifications to determine if they are of another serotype according to the traditional definition of serotype. Accordingly, for the sake of convenience and to avoid repetition, the term "serotype" broadly refers to both serologically distinct viruses (e.g., AAV) as well as viruses (e.g., AAV) that are not serologically distinct that may be within a subgroup or variant of a given serotype.

By way of example, AAV include various naturally and non-naturally occurring serotypes. Such non-limiting serotypes include AAV-1, -2, -3, -4, -5, -6, -7, -8, -9, -10, -11, -rh74, -rh10 and AAV-2i8. Again, for the sake of convenience serotypes include AAV with capsid sequence modifications that have not been fully characterized as being a distinct serotype, and may in fact actually constitute a subgroup or variant of a known serotype.

AAV vectors, empty capsids, genome containing capsids and capsid proteins as set forth herein include those having a polynucleotide, polypeptide or subsequence thereof that includes or consists of a sequence at least 80% or more (e.g., 85%, 90%, 95%, 96%, 97%, 98%, 99%, 99.5%, etc.) identical to any of AAV1, AAV2, AAV3, AAV4, AAV5, AAV6, AAV7, AAV8, AAV9, AAV10, AAV11, Rh10, Rh74 or AAV-2i8 VP1, VP2, and/or VP3 capsid sequences. Such capsid sequences for AAV1, AAV2, AAV3, AAV4, AAV5, AAV6, AAV7, AAV8, AAV9, AAV10, AAV11, Rh10, Rh74 or AAV-2i8 are known in the art.

AAV vectors, empty capsids, genome containing capsids, including AAV1, AAV2, AAV3, AAV4, AAV5, AAV6, AAV7, AAV8, AAV9, AAV10, AAV11, Rh10, Rh74 or AAV-2i8 and sequence related AAV vectors, can be constructed using recombinant techniques that are known to the skilled artisan, to include one or more heterologous polynucleotide sequences (transgenes) flanked with functional AAV ITRs. Incorporation of a heterologous polynucleotide defines the AAV as a recombinant vector, which can be referred to as an "rAAV vector." Such vectors can have one or more of the wild type AAV genes deleted in whole or in part, for example, a rep and/or cap gene, but retain at least one functional flanking ITR sequence, as necessary for the rescue, replication, and packaging of the AAV vector particle. Thus, an AAV vector includes sequences required in cis for viral replication and packaging (e.g., functional ITRs).

"Cross-linking" is a chemical, physical, or biological procedure used to establish covalent bonds between protein chains otherwise separate. Non-limiting examples include formaldehyde treatment, and derivatization with bifunctional agents. Commonly used cross linking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 5 mM 3,3'-Dithiobis (sulfosuccinimidylpropionate) (DTSSP), 3,3'-dithiobis(succinimidylpropionate), bifunctional maleimides such as bis-N-maleimido-1,8-octane and agents such as methyl-3-[(p-azidophenyl)dithio]propioimidate. Empty capsids, genome (e.g., viral) containing capsids and capsid proteins in accordance with the invention can be cross-linked, and the cross-linked capsids or capsid proteins can be a component of a vector formulation.

The terms "polynucleotide" and "nucleic acid" are used interchangeably herein to refer to all forms of nucleic acid, oligonucleotides, including deoxyribonucleic acid (DNA) and ribonucleic acid (RNA). Polynucleotides include genomic DNA, cDNA and antisense DNA, and spliced or unspliced mRNA, rRNA tRNA and inhibitory DNA or RNA (RNAi, e.g., small or short hairpin (sh)RNA, microRNA (miRNA), small or short interfering (si)RNA, trans-splicing RNA, or antisense RNA). Polynucleotides include naturally occurring, synthetic, and intentionally altered or modified polynucleotides as well as analogues and derivatives. Polynucleotides can be single, double, or triplex, linear or circular, and can be of any length.

A "heterologous" polynucleotide merely refers to a polynucleotide inserted into AAV for purposes of AAV mediated transfer/delivery of the polynucleotide into a cell. Heterologous polynucleotides are typically distinct from AAV nucleic acid, i.e., are "non-native" with respect to AAV nucleic acid. Once transferred/delivered into the cell, a heterologous polynucleotide, contained within the rAAV virion, can be expressed (e.g., transcribed, and translated if appropriate). Alternatively, a transferred/delivered heterologous polynucleotide in a cell, contained within the rAAV virion, need not be expressed. Although the term "heterologous" is not always used herein in reference to polynucleotides, reference to a polynucleotide even in the absence of the modifier "heterologous" includes heterologous polynucleotides in spite of the omission.

The "polypeptides," "proteins" and "peptides" encoded by "polynucleotide sequences," include full-length native sequences, as with naturally occurring proteins, as well as functional subsequences, modified forms or sequence variants so long as the subsequence, modified form or variant retains some degree of functionality of the native full-length protein. In methods and uses of the invention, such polypeptides, proteins and peptides encoded by the polynucleotide sequences can be but are not required to be identical to the endogenous protein that is defective, or whose expression is insufficient, or deficient in the treated mammal.

Viral (e.g., AAV) vectors can be used to introduce/deliver polynucleotides stably or transiently into cells and progeny thereof. The term "transgene" is used to conveniently refer to such a heterologous polynucleotide that can be introduced into a cell or organism by way of a viral vector. Transgenes broadly include any polynucleotide, such as a gene that encodes a polypeptide or protein, a polynucleotide that is transcribed into an inhibitory polynucleotide (e.g., siRNA, miRNA, shRNA), or a polynucleotide that is not transcribed (e.g., lacks a expression control element, such as a promoter that drives transcription). For example, in a cell having a transgene, the transgene has been introduced/transferred by vector (e.g., AAV) mediated "transformation" of the cell. A cell, or progeny thereof, into which the transgene has been introduced is referred to as a "transformed cell" or "transformant" Typically, a transgene is included in progeny of the transformant or becomes a part of the organism that develops from the cell. Accordingly, a "transformed" or "transfected" cell (e.g., in a mammal, such as a cell or tissue or organ cell), means a genetic change in a cell following incorporation of an exogenous molecule, for example, a polynucleotide or protein (e.g., a transgene) into the cell. Thus, a "transfected" or "transformed" cell is a cell into which, or a progeny thereof in which an exogenous molecule has been introduced, for example. The cell(s) can be propagated and the introduced protein expressed, or nucleic acid transcribed.

Cells that may be transformed include a cell of any tissue or organ type, of any origin (e.g., mesoderm, ectoderm or endoderm). Non-limiting examples of cells include liver (e.g., hepatocytes, sinusoidal endothelial cells), pancreas (e.g., beta islet cells), lung, central or peripheral nervous system, such as brain (e.g., neural, glial or ependymal cells) or spine, kidney, eye (e.g., retinal, cell components), spleen, skin, thymus, testes, lung, diaphragm, heart (cardiac), muscle or psoas, or gut (e.g., endocrine), adipose tissue (white, brown or beige), muscle (e.g., fibroblasts), synoviocytes, chondrocytes, osteoclasts, epithelial cells, endothelial cells, salivary gland cells, inner ear nervous cells or hematopoietic (e.g., blood or lymph) cells. Additional examples include stem cells, such as pluripotent or multipotent progenitor cells that develop or differentiate into liver (e.g., hepatocytes, sinusoidal endothelial cells), pancreas (e.g., beta islet cells), lung, central or peripheral nervous system, such as brain (e.g., neural, glial or ependymal cells) or spine, kidney, eye (retinal, cell components) spleen, skin, thymus, testes, lung, diaphragm, heart (cardiac), muscle or psoas, or gut (e.g., endocrine), adipose tissue (white, brown or beige), muscle (e.g., fibroblasts), synoviocytes, chondrocytes, osteoclasts, epithelial cells, endothelial cells, salivary gland cells, inner ear nervous cells or hematopoietic (e.g., blood or lymph) cells.

A "therapeutic molecule" in one embodiment is a peptide or protein that may alleviate or reduce symptoms that result from an absence or defect in a protein in a cell or subject. Alternatively, a "therapeutic" peptide or protein encoded by a transgene is one that confers a benefit to a subject, e.g., to correct a genetic defect, to correct a gene (expression or functional) deficiency, or an anti-cancer effect. Therapeutic peptides and proteins include, but are not limited to, cystic fibrosis transmembrane regulator protein (CFTR), dystrophin, utrophin, blood coagulation (clotting) factor (e.g., Factor XIII, Factor IX, Factor X, Factor VIII, Factor VIIa, protein C, Factor VII, B domain-deleted Factor VIII, or a high-activity or longer half life variant of coagulation factor, or an active or inactive form of a coagulation factor), a monoclonal antibody, retinal pigment epithelium-specific 65 kDa protein (RPE65), erythropoietin, LDL receptor, lipoprotein lipase, ornithine transcarbamylase, β-globin, α-globin, spectrin, α-antitrypsin, adenosine deaminase (ADA), a metal transporter (ATP7A or ATP7), sulfamidase, an enzyme involved in lysosomal storage disease (ARSA), hypoxanthine guanine phosphoribosyl transferase, β-25 glucocerebrosidase, sphingomyelinase, lysosomal hexosaminidase, branched-chain keto acid dehydrogenase, a hormone, a growth factor, insulin-like growth factor 1 or 2, platelet derived growth factor, epidermal growth factor, nerve growth factor, neurotrophic factor-3 and -4, brain-derived neurotrophic factor, glial derived growth factor, transforming growth factor α and β, a cytokine, α-interferon, β-interferon, interferon-γ, interleukin-2, interleukin-4, interleukin-12, granulocyte-macrophage colony stimulating factor, lymphotoxin, a suicide gene product, herpes simplex virus thymidine kinase, cytosine deaminase, diphtheria toxin, cytochrome P450, deoxycytidine kinase, tumor necrosis factor, a drug resistance protein, a tumor suppressor protein (e.g., p53, Rb, Wt-1, NF1, Von Hippel-Lindau (VHL), SERCA2a, adenomatous polyposis coli (APC)), VEGF, microdystrophin, lysosomal acid lipase, arylsulfatase A and B, ATP7A and B, a peptide with immunomodulatory properties, a tolerogenic or immunogenic peptide or protein Tregitope or hCDR1, insulin, glucokinase, guanylate cyclase 2D (LCA-GUCY2D), Rab escort protein 1 (Choroideremia), LCA 5 (LCA-Lebercilin), ornithine ketoacid aminotransferase (Gyrate Atrophy), Retinoschisis 1 (X-linked Retinoschisis), USH1C (Usher's Syndrome 1C), X-linked retinitis pigmentosa GTPase (XLRP), MERTK (AR forms of RP: retinitis pigmentosa), DFNB1 (Connexin 26 deafness), ACHM 2, 3 and 4 (Achromatopsia), PKD-1 or PKD-2 (Polycystic kidney disease), TPP1, CLN2, a gene product implicated in lysosomal storage diseases (e.g., sulfatases, N-acetylglucosamine-1-phosphate transferase, cathepsin A, GM2-AP, NPC1, VPC2, a sphingolipid activator protein, or one or more zinc finger nucleases for genome editing, or donor sequences used as repair templates for genome editing, and any other peptide or protein that has a therapeutic effect in a subject in need thereof.

Further exemplary therapeutic peptides or proteins encoded by transgenes include those that may be used in the treatment of a disease or disorder including, but not limited to, cystic fibrosis (and other diseases of the lung), hemophilia A, hemophilia B, thalassemia, anemia and other blood disorders, AIDS, Alzheimer's disease, Parkinson's disease, Huntington's disease, amyotrophic lateral sclerosis, epilepsy, and other neurological disorders, cancer, diabetes mellitus, muscular dystrophies (e.g., Duchenne, Becker), Gaucher's disease, Hurler's disease, adenosine deaminase deficiency, glycogen storage diseases and other metabolic defects, retinal degenerative diseases (and other diseases of the eye), and diseases of solid organs (e.g., brain, liver, kidney, heart).

As set forth herein, polynucleotide sequences (transgenes) include inhibitory and antisense nucleic acid sequences Inhibitory, antisense, siRNA, miRNA, shRNA, RNAi and antisense oligonucleotides can modulate expression of a target gene. Such molecules include those able to inhibit expression of a target gene involved in mediation of a disease process, thereby reducing, inhibiting or alleviating one or more symptoms of a disease.

Antisense includes single, double or triple stranded polynucleotides and peptide nucleic acids (PNAs) that bind RNA transcript or DNA (e.g., genomic DNA). Oligonucleotides derived from the transcription initiation site of a target gene, e.g., between positions −10 and +10 from the start site, are another particular example. Triplex forming antisense can bind to double strand DNA thereby inhibiting transcription of the gene. "RNAi" is the use of single or double stranded RNA sequences for inhibiting gene expression (see, e.g., Kennerdell et al., Cell 95:1017 (1998); and Fire et al., Nature, 391:806 (1998)). Double stranded RNA sequences from a target gene coding region may therefore be used to inhibit or prevent gene expression/transcription in accordance with the methods and uses of the invention. Antisense and RNAi can be produced based upon nucleic acids encoding target gene sequences (e.g., HTT), such as nucleic acid encoding mammalian and human HTT. For example, a single or double stranded nucleic acid (e.g., RNA) can target HTT transcript (e.g., mRNA).

A "siRNA" refers to a therapeutic molecule involved in the RNA interference process for a sequence-specific post-transcriptional gene silencing or gene knockdown. siRNAs have homology with the sequence of the cognate mRNA of the targeted gene. Small interfering RNAs (siRNAs) can be synthesized in vitro or generated by ribonuclease III cleavage from longer dsRNA and are the mediators of sequence-specific mRNA degradation. siRNA or other such nucleic acids of the invention can be chemically synthesized using appropriately protected ribonucleoside phosphoramidites and a conventional DNA/RNA synthesizer. The siRNA can be synthesized as two separate, complementary RNA molecules, or as a single RNA molecule with two complementary regions. Commercial suppliers of synthetic RNA molecules or synthesis reagents include Applied Biosystems (Foster City, Calif., USA), Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK). Specific siRNA constructs for inhibiting mRNA of a target gene may be between 15-50 nucleotides in length, and more typically about 20-30 nucleotides in length. Such nucleic acid molecules can be readily incorporated into the viral vectors disclosed herein using conventional methods known to one of skill in the art.

Particular non-limiting examples of genes (e.g., genomic DNA) or transcript of a pathogenic gene (e.g., RNA or mRNA) that may be targeted with inhibitory nucleic acid sequences in accordance with the invention include, but are not limited to: pathogenic genes associated with polynucleotide repeat diseases such as huntingtin (HTT) gene, a gene associated with dentatorubropallidolusyan atropy (e.g., atrophin 1, ATN1); androgen receptor on the X chromosome in spinobulbar muscular atrophy, human Ataxin-1, -2, -3, and -7, $Ca_v2.1$ P/Q voltage-dependent calcium channel in encoded by the (CACNA1A), TATA-binding protein, Ataxin 8 opposite strand, also known as ATXN8OS, Serine/threonine-protein phosphatase 2A 55 kDa regulatory subunit B beta isoform in spinocerebellar ataxia (type 1, 2, 3, 6, 7, 8, 12 17), FMR1 (fragile X mental retardation 1) in fragile X syndrome, FMR1 (fragile X mental retardation 1) in fragile X-associated tremor/ataxia syndrome, FMR1 (fragile X mental retardation 2) or AF4/FMR2 family member 2 in fragile XE mental retardation; Myotonin-protein kinase (MT-PK) in myotonic dystrophy; Frataxin in Friedreich's ataxia; a mutant of superoxide dismutase 1 (SOD1) gene in amyotrophic lateral sclerosis; a gene involved in pathogenesis of Parkinson's disease and/or Alzheimer's disease; apolipoprotein B (APOB) and proprotein convertase subtilisin/kexin type 9 (PCSK9), hypercoloesterolemia; HIV Tat, human immunodeficiency virus transactivator of transcription gene, in HIV infection; HIV TAR, HIV TAR, human immunodeficiency virus transactivator response element gene, in HIV infection; C—C chemokine receptor (CCR5) in HIV infection; Rous sarcoma virus (RSV) nucleocapsid protein in RSV infection, liver-specific microRNA (miR-122) in hepatitis C virus infection; p53, acute kidney injury or delayed graft function kidney transplant or kidney injury acute renal failure; protein kinase N3 (PKN3) in advance recurrent or metastatic solid malignancies; LMP2, LMP2 also known as proteasome subunit beta-type 9 (PSMB 9), metastatic melanoma; LMP7, also known as proteasome subunit beta-type 8 (PSMB 8), metastatic melanoma; MECL1 also known as proteasome subunit beta-type 10 (PSMB 10), metastatic melanoma; vascular endothelial growth factor (VEGF) in solid tumors; kinesin spindle protein in solid tumors, apoptosis suppressor B-cell CLL/lymphoma (BCL-2) in chronic myeloid leukemia; ribonucleotide reductase M2 (RRM2) in solid tumors; Furin in solid tumors; polo-like kinase 1 (PLK1) in liver tumors, diacylglycerol acyltransferase 1 (DGAT1) in hepatitis C infection, beta-catenin in familial adenomatous polyposis; beta2 adrenergic receptor, glaucoma; RTP801/Redd1 also known as DAN damage-inducible transcript 4 protein, in diabetic macular edema (DME) or age-related macular degeneration; vascular endothelial growth factor receptor I (VEGFR1) in age-related macular degeneration or choroidal neivascularization, caspase 2 in non-arteritic ischaemic optic neuropathy; Keratin 6A N17K mutant protein in pachyonychia congenital; influenza A virus genome/gene sequences in influenza infection; severe acute respiratory syndrome (SARS) coronavirus genome/gene sequences in SARS infection; respiratory syncytial virus genome/gene sequences in respiratory syncytial virus infection; Ebola filovirus genome/gene sequence in Ebola infection; hepatitis B and C virus genome/gene sequences in hepatitis B and C infection; herpes simplex virus (HSV) genome/gene sequences in HSV infection, coxsackievirus B3 genome/gene sequences in coxsackievirus B3 infection; silencing of a pathogenic allele of a gene (allele-specific silencing) like torsin A (TOR1A) in primary dystonia, pan-class I and HLA-allele specific in transplant; or mutant rhodopsin gene (RHO) in autosomal dominantly inherited retinitis pigmentosa (adRP).

As used herein, the term "recombinant," as a modifier of viral vector, such as recombinant AAV vectors, as well as a modifier of sequences such as recombinant polynucleotides and polypeptides, means that the compositions have been manipulated (i.e., engineered) in a fashion that generally does not occur in nature. A particular example of a recombinant AAV would be where a polynucleotide that is not normally present in the wild-type AAV is within the AAV particle and/or genome. For example, a particular example of a recombinant polynucleotide would be where a polynucleotide (e.g., transgene) encoding a protein is cloned into a vector, with or without 5', 3' and/or intron regions that the gene is normally associated within the AAV genome. Although the term "recombinant" is not always used herein in reference to AAV vectors, as well as sequences such as polynucleotides and polypeptides, recombinant forms of AAV and AAV vectors, and sequences including polynucleotides and polypeptides, are expressly included in spite of any such omission.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

Expression control can be effected at the level of transcription, translation, splicing, message stability, etc. The term "expression control element" refers to one or more nucleic acid sequence elements that regulate or influence expression of a nucleic acid sequence to which it is operatively linked. An expression control element can include, as appropriate, promoters, enhancers, transcription terminators, gene silencers, a start codon (e.g., ATG) in front of a protein-encoding gene, etc. Typically, an expression control element that modulates transcription is juxtaposed near the 5' end of the transcribed transgene (i.e., "upstream"). Expression control elements can also be located at the 3' end of the transcribed sequence (i.e., "downstream") or within the transcript (e.g., in an intron). Expression control elements can be located at a distance away from the transcribed transgene (e.g., 100 to 500, 500 to 1000, 2000 to 5000, 5000 to 10,000 or more nucleotides from the polynucleotide), even at considerable distances. Nevertheless, owing to the polynucleotide length limitations, for AAV vectors, such expression control elements will typically be within 1 to 1000 nucleotides from the transgene.

An expression control element operatively linked to a nucleic acid sequence controls transcription and, as appropriate, translation of the nucleic acid sequence. The term "operatively linked" refers to a juxtaposition wherein the referenced components are in a relationship permitting them to function in their intended manner Typically, expression control elements are juxtaposed at the 5' or the 3' ends of the genes but can also be intronic.

Expression control elements and promoters include those active in a particular tissue or cell type, referred to herein as a "tissue-specific expression control elements/promoters." Tissue-specific expression control elements are typically active in specific cell or tissue (e.g., liver, brain, central nervous system, spinal cord, eye, retina or lung). Expression control elements are typically active in these cells, tissues or organs because they are recognized by transcriptional activator proteins, or other regulators of transcription, that are unique to a specific cell, tissue or organ type.

Expression control elements also can confer expression in a manner that is regulatable, that is, a signal or stimuli increases or decreases expression of the operably linked polynucleotide. A regulatable element that increases expression of the operably linked polynucleotide in response to a signal or stimuli is also referred to as an "inducible element" (i.e., is induced by a signal). Particular examples include, but are not limited to, a hormone (e.g., steroid) inducible promoter. A regulatable element that decreases expression of the operably linked polynucleotide in response to a signal or stimuli is referred to as a "repressible element" (i.e., the signal decreases expression such that when the signal, is removed or absent, expression is increased). Typically, the amount of increase or decrease conferred by such elements is proportional to the amount of signal or stimuli present; the greater the amount of signal or stimuli, the greater the increase or decrease in expression.

The term "promoters" or "promoter" as used herein can refer to a DNA sequence that is located adjacent to a DNA sequence that encodes a recombinant product. A promoter is preferably linked operatively to an adjacent DNA sequence. A promoter typically increases an amount of recombinant product expressed from a DNA sequence as compared to an amount of the expressed recombinant product when no promoter exists. A promoter from one organism can be utilized to enhance recombinant product expression from a DNA sequence that originates from another organism. For example, a vertebrate promoter may be used for the expression of jellyfish GFP in vertebrates. In addition, one promoter element can increase an amount of recombinant products expressed for multiple DNA sequences attached in tandem. Hence, one promoter element can enhance the expression of one or more recombinant products. Multiple promoter elements are well-known to persons of ordinary skill in the art.

In one embodiment, high-level constitutive expression is desired. Such expression control elements include ubiquitous or promiscuous promoters/enhancers which are capable of driving expression of a transgene in many different cell types. Such elements include, but are not limited to the cytomegalovirus (CMV) immediate early promoter/enhancer sequences, the Rous sarcoma virus (RSV) promoter/enhancer sequences and the other viral promoters/enhancers active in a variety of mammalian cell types, or synthetic elements that are not present in nature (see, e.g., Boshart et al. Cell, 41:521-530 (1985)), the SV40 promoter, the dihydrofolate reductase promoter, the cytoplasmic β-actin promoter and the phosphoglycerol kinase (PGK) promoter.

In another embodiment, inducible promoters may be desired. Inducible promoters are those which are regulated by exogenously supplied compounds, either in cis or in trans, including without limitation, the zinc-inducible sheep metallothionine (MT) promoter; the dexamethasone (Dex)-inducible mouse mammary tumor virus (MMTV) promoter; the T7 polymerase promoter system (WO 98/10088); the tetracycline-repressible system (Gossen, et al., *Proc. Natl. Acad. Sci.* USA, 89:5547-5551 (1992)); the tetracycline-inducible system (Gossen, et al., *Science*. 268:1766-1769 (1995); see also Harvey, et al., *Curr. Opin. Chem. Biol.* 2:512-518 (1998)); the RU486-inducible system (Wang, et al., *Nat. Biotech.* 15:239-243 (1997) and Wang, et al., *Gene Ther.* 4:432-441 (1997)]; and the rapamycin-inducible system (Magari, et al., *J. Clin. Invest.* 100:2865-2872 (1997); Rivera, et al., *Nat. Medicine.* 2:1028-1032 (1996)). Other types of inducible promoters which may be useful in this context are those which are regulated by a specific physiological state, e.g., temperature, acute phase, or in replicating cells only.

In another embodiment, the native promoter for the transgene or nucleic acid sequence of interest will be used. The native promoter may be preferred when it is desired that expression of the transgene or the nucleic acid sequence should mimic the native expression. The native promoter may be used when expression of the transgene or other nucleic acid sequence must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In one embodiment, the recombinant viral genome comprises a transgene operably linked to a tissue-specific promoter (e.g., a promoter that is active in a cell or tissue such as liver, bone, muscle, retinal cells, brain or neural tissue, pancreas, heart, kidney, etc.). For instance, if expression in skeletal muscle is desired, a promoter active in muscle may be used. These include the promoters from genes encoding skeletal α-actin, myosin light chain 2A, dystrophin, muscle creatine kinase, as well as synthetic muscle promoters with activities higher than naturally-occurring promoters. See Li, et al., *Nat. Biotech.* 17:241-245 (1999). Examples of promoters that are tissue-specific are known for liver albumin, Miyatake, et al. *J. Virol.*, 71:5124-32 (1997); hepatitis B virus core promoter, Sandig, et al., *Gene Ther.* 3:1002-9 (1996); alpha-fetoprotein (AFP), Arbuthnot, et al., *Hum. Gene. Ther.*, 7:1503-14 (1996)], bone (osteocalcin, Stein, et al., *Mol. Biol. Rep.*, 24:185-96 (1997); bone sialoprotein, Chen, et al., *J. Bone Miner. Res.* 11:654-64 (1996)), lymphocytes (CD2, Hansal, et al., *J. Immunol.*, 161:1063-8 (1998); immunoglobulin heavy chain; T cell receptor a chain), neuronal (neuron-specific enolase (NSE) promoter, Andersen, et al., *Cell. Mol. Neurobiol.*, 13:503-15 (1993); neurofilament light-chain gene, Piccioli, et al., *Proc. Natl. Acad. Sci.* USA, 88:5611-5 (1991); the neuron-specific vgf gene, Piccioli, et al., *Neuron*, 15:373-84 (1995)]; among others. Synthetic promoters, obtained by combination of elements from different promoters or by development of synthetic DNA sequences, can also be used.

The term "enhancers" or "enhancer" as used herein can refer to a DNA sequence that is located adjacent to the DNA sequence that encodes a recombinant product Enhancer elements are typically located upstream of a promoter element or can be located downstream of or within a coding DNA sequence (e.g., a DNA sequence transcribed or translated into a recombinant product or products). Hence, an enhancer element can be located 100 base pairs, 200 base pairs, or 300 or more base pairs upstream or downstream of a DNA sequence that encodes recombinant product. Enhancer elements can increase an amount of recombinant product expressed from a DNA sequence above increased expression afforded by a promoter element. Multiple enhancer elements are readily available to persons of ordinary skill in the art.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

A "vector" is a replicon, such as a plasmid, cosmid, bacmid, phage or virus (e.g., AAV vector), to which another genetic sequence or element (either DNA or RNA) may be attached so as to bring about the replication of the attached sequence or element.

The terms "transform", "transfect", "transduce", refer to any method or means by which a nucleic acid (transgene) is introduced into a cell or host organism and may be used interchangeably to convey the same meaning. For gene therapy uses and methods, a transformed cell can be in a subject. A cell in a subject can be transformed with a transgene as set forth herein in vivo. Alternatively, a cell can be transformed in vitro with a transgene, and then transplanted into a tissue of subject in order to effect treatment. Alternatively, a primary cell isolate or an established cell line can be transformed with a transgene, and then optionally transplanted into a tissue of a subject. Such methods include, but are not limited to, transfection, electroporation, microinjection, infection, PEG-fusion and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid (genomic DNA) of the recipient cell or organism and be stably maintained in that cell or organism and further passed on to or inherited by progeny cells or organisms of the recipient cell or organism. Finally, the introduced nucleic acid may exist in the recipient cell or host organism only transiently.

The term "selectable marker gene" refers to a gene that when expressed confers a selectable phenotype, such as antibiotic resistance, on a transformed cell or plant. A "reporter" gene is one that provides a detectable signal. A non-limiting example of a reporter gene is the luciferase gene.

The term "operably linked" means that the regulatory sequences necessary for expression of the coding sequence are placed in the DNA molecule in the appropriate positions relative to the trangene (e.g., protein coding sequence or inhibitory nucleic acid) so as to effect expression of the transgene sequence. This same definition is sometimes applied to the arrangement of transcription units and other transcription control elements (e.g. enhancers) in an expression vector.

The term "oligonucleotide" as used herein refers to sequences, primers and probes of the invention, and is defined as a nucleic acid molecule comprised of two or more ribo- or deoxyribonucleotides, preferably more than three. The exact size of the oligonucleotide will depend on various factors and on the particular application and use of the oligonucleotide.

The phrase "specifically hybridize" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "primer" as used herein refers to a DNA oligonucleotide, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

The term "isolated" may refer to a compound or complex that has been sufficiently separated from other compounds with which it would naturally be associated. "Isolated" is not meant to exclude artificial or synthetic mixtures with other compounds or materials, or the presence of impurities that do not interfere with fundamental activity or ensuing assays, and that may be present, for example, due to incomplete purification, or the addition of stabilizers.

The term "immune response" is meant to refer to any response to an antigen or antigenic determinant by the immune system of a vertebrate subject. Exemplary immune responses include humoral immune responses (e.g. production of antigen-specific antibodies) and cell-mediated immune responses (e.g. lymphocyte activation or proliferation).

Methods of the invention provide a means for delivering (transducing) heterologous nucleic acid sequences (transgenes) into a broad range of host cells, including both dividing and non-dividing cells. The vectors and other reagents, methods and pharmaceutical formulations of the invention are additionally useful in a method of administering a protein, peptide or therapeutic nucleic acid to a subject in need thereof, as a method of treatment. In this manner, the protein, peptide or nucleic acid may thus be produced in vivo in the subject. The subject may benefit from or be in need of the protein or peptide because the subject has a deficiency of the protein or peptide, or because the production of the protein or peptide in the subject may impart some therapeutic effect, as a method of treatment or otherwise. Alternatively, it may be desirable to inhibit or reduce expression or production of a target gene involved in a disease process, e.g., for the treatment of cancer or atherosclerosis or a neurodegenerative disease, for example to achieve a therapeutic effect.

In general, invention formulations, methods and uses may be used to deliver any nucleic acid (transgene) with a biological effect to treat or ameliorate the symptoms associated with any disorder related to gene expression. Illustrative disease states include, but are not limited to: cystic fibrosis (and other diseases of the lung), hemophilia A, hemophilia B, thalassemia, anemia and other blood coagulation disorders, AIDs, Alzheimer's disease, Parkinson's disease, Huntington's disease, amyotrophic lateral sclerosis, epilepsy, and other neurological disorders, cancer, diabetes mellitus, muscular dystrophies (e.g., Duchenne, Becker), Gaucher's disease, Hurler's disease, adenosine deaminase deficiency, glycogen storage diseases and other metabolic defects, Pompe's disease, congestive heart failure, retinal degenerative diseases (and other diseases of the eye), diseases of solid organs (e.g., brain, liver, kidney, heart), and the like.

In addition, invention formulations, methods and uses may be employed to deliver nucleic acids encoding monoclonal antibodies or fragments thereof that are known to provide beneficial biological effects to treat or ameliorate the symptoms associated with cancers, infectious diseases, and autoimmune diseases such as rheumatoid arthritis.

Gene transfer is used to provide therapy for various disease states. There are a number of inherited diseases in which defective genes are known and have been cloned. In some cases, the function of these cloned genes is known. In general, the above disease states fall into two classes: deficiency states, usually of enzymes, which are generally inherited in a recessive manner, and unbalanced states, at least sometimes involving regulatory or structural proteins, which are inherited in a dominant manner. For deficiency state diseases, gene transfer could be used to bring a normal gene into affected tissues for replacement therapy, as well as to create animal models for the disease using antisense mutations. For unbalanced disease states, gene transfer could be used to create a disease state in a model system, which could then be used in efforts to counteract the disease state. Thus invention formulations, methods and uses permit the treatment of genetic diseases. As used herein, a disease state is treated by partially or wholly remedying the deficiency or imbalance that causes the disease or makes it more severe. The use of site-specific integration of nucleic acid sequences to cause mutations or to correct defects is also possible.

The invention is useful in both human and veterinary medical applications. Suitable subjects include mammals, such as humans. The term "mammal" as used herein includes, but is not limited to, humans, bovines, ovines, caprines, equines, felines, canines, lagomorphs, etc. Human subjects are the most preferred. Human subjects include fetal, neonatal, infant, juvenile and adult subjects.

In particular embodiments, the invention provides a pharmaceutical composition comprising a vector and/or empty or genome (e.g., viral) containing capsids in a pharmaceutically-acceptable carrier or other medicinal agents, pharmaceutical agents, carriers, adjuvants, diluents, etc. For injection, the carrier will typically be a liquid. For other methods of administration, the carrier may be either solid or liquid, such as sterile, pyrogen-free water or sterile pyrogen-free phosphate-buffered saline solution. For inhalation administration, the carrier will be respirable, and will preferably be in solid or liquid particulate form. As an injection medium, water that contains the additives usual for injection solutions, such as stabilizing agents, salts or saline, and/or buffers may be included.

In other embodiments, the invention provides a pharmaceutical composition comprising a cell in which an AAV provirus is integrated into the genome in a pharmaceutically-acceptable carrier or other medicinal agents, pharmaceutical agents, carriers, adjuvants, diluents, etc. Such cells can be produced in vivo, in vitro or ex vivo.

By "pharmaceutically acceptable" it is meant a material that is not biologically or otherwise undesirable, e.g., the material may be administered to a subject without causing any undesirable biological effects. Thus, such a pharmaceutical composition may be used, for example in administering a viral particle or cell directly to a subject typically via intravenous administration.

A "therapeutically-effective" amount as used herein is an amount that is sufficient to alleviate (e.g., mitigate, decrease, reduce) at least one of the symptoms associated with a disease state. Alternatively stated, a "therapeutically-effective" amount is an amount that is sufficient to provide some improvement in the condition of the subject.

A further aspect of the invention is a method of administration or treating subjects in vivo with the inventive formulations described herein. Administration of the vectors separately or in combination with empty capsids or genome (e.g., viral) containing capsids or capsid proteins to a subject (e.g., human) or an animal in need thereof can be by any means known in the art for administering virus vectors.

Exemplary modes of administration include orally (e.g., ingestion, buccal, or sublingual), rectal, transmucosal, topical, transdermal (topical), inhalation, parenteral (e.g., intravenous, subcutaneous, intradermal, intramuscular, and intraarticular) intracavity, intracranially, intra-spinal, administration, and the like, as well as direct tissue or organ injection (intraglandular, intraorgan, intralymphatic, intrapulmonary), alternatively, intrathecal, direct intramuscular, intraventricular, intravenous, intraperitoneal, intranasal, endomyocardial, intraocular injections or intravascular delivery. Alternatively, one may administer the virus in a local rather than systemic manner, for example.

In particular embodiments of the invention, the transgene is delivered to the liver of the subject. Administration to the liver may be achieved by any method known in art, including, but not limited to intravenous administration, intraportal administration, intrabilary administration, intra-arterial administration, and direct injection into the liver paraenchyma.

The cells (e.g., liver cells, such as hepatocytes) are infected by a recombinant parvovirus vector encoding a peptide, protein or therapeutic nucleic acid, the cells express the encoded peptide, protein or therapeutic nucleic acid and secrete it into the circulatory system in a therapeutically-effective amount. Alternatively, the vector is delivered to and expressed by another cell or tissue, including but not limited to, brain, pancreas, spleen or muscle.

The vector dose to achieve a therapeutic effect, e.g., the dose in vector genomes/per kilogram of body weight (vg/kg), or transducing units will vary based on several factors including, but not limited to: route of administration, the level of transgene expression required to achieve a therapeutic effect, the specific disease treated, any host immune response to the vector (e.g., AAV), a host immune response to the transgene or expression product (protein), and the stability of the protein expressed. One skilled in the art can readily determine a AAV vector dose range to treat a patient having a particular disease or disorder based on the aforementioned factors, as well as other factors. Generally, doses will range from at least $1\times10^6$, $1\times10^7$, $1\times10^8$, or more, for example, $1\times10^9$, $1\times10^{10}$, $1\times10^{11}$, $1\times10^{12}$, $1\times10^{13}$ or $1\times10^{14}$, $1\times10^{15}$, $1\times10^{16}$, or more, vector genomes per kilogram (vg/kg) of the weight of the subject, to achieve a therapeutic effect.

In particular embodiments of the invention, more than one administration (e.g., two, three, four, or more administrations) may be employed to achieve therapeutic levels of transgene expression. According to this embodiment and as described herein the parvovirus formulations of the invention are administered to circumvent neutralizing antibodies in the subject to be treated.

The titer of neutralizing antibodies (NAbs) specific to AAV vectors can be measured with an in vitro assay in which test serum will be incubated with an AAV vector having a reporter transgene and used to transduce cells. The residual reporter gene activity in vitro will be used to determine the extent of neutralization of AAV vector-specific NAb. Subjects with high-titer NAb may be administered with a large excess (10 to 10,000-fold capsid particle concentration in excess of the AAV vector dose) of AAV empty capsids; subjects with low to negative titer NAb can receive lower amounts of empty capsids (1 to 10-fold capsid particle concentration n excess of the AAV vector dose).

As disclosed herein, empty or genome (e.g., viral) containing capsids or capsid proteins can be either untreated or modified to reduce intracellular uptake, cross-linked or modified by mutating one or more amino acid residues (e.g., of a capsid protein) to reduce receptor binding (e.g., binding to heparan sulfate proteoglycan). The AAV vector may be formulated with the empty or genome (e.g., viral) containing capsids or capsid proteins and administered to the subject as a combination, or the AAV vector and empty or genome (e.g., viral) containing capsids or capsid proteins may be administered separately from each other to the subject.

In summary, parvovirus vectors, reagents, and methods and uses of the invention can be used to direct a transgene to either dividing or non-dividing cells, and to stably express the nucleic acid therein. The vectors of the invention can thus be useful in gene therapy for disease states or for experimental modification of cell physiology.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All applications, publications, patents and other references, GenBank citations and ATCC citations cited herein are incorporated by reference in their entirety. In case of conflict, the specification, including definitions, will control.

All of the features disclosed herein may be combined in any combination. Each feature disclosed in the specification may be replaced by an alternative feature serving a same, equivalent, or similar purpose. Thus, unless expressly stated otherwise, disclosed features (e.g., compound structures) are an example of a genus of equivalent or similar features.

As used herein, the singular forms "a", "and," and "the" include plural referents unless the context clearly indicates otherwise. Thus, for example, reference to "a polynucleotide" includes a plurality of such polynucleotides, such as a plurality of genes.

As used herein, all numerical values or numerical ranges include integers within such ranges and fractions of the values or the integers within ranges unless the context clearly indicates otherwise. Thus, to illustrate, reference to at least 90% identity, includes 91%, 92%, 93%, 94%, 95%, 95%, 97%, 98%, 99%, etc., as well as 91.1%, 91.2%, 91.3%, 91.4%, 91.5%, etc., 92.1%, 92.2%, 92.3%, 92.4%, 92.5%, etc., and so forth.

Reference to a number with more (greater) or less than includes any number greater or less than the reference number, respectively. Thus, for example, a reference to less than 1,000, includes 999, 998, 997, etc. all the way down to the number one (1); and less than 100, includes 99, 98, 97, etc. all the way down to the number one (1).

As used herein, all numerical values or ranges include fractions of the values and integers within such ranges and fractions of the integers within such ranges unless the context clearly indicates otherwise. Thus, to illustrate, reference to a numerical range, such as a percentage range, 90-100%, includes 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, etc., and so forth. Reference to a range of 1-50 therefore includes 1, 2, 3, 4, 5, 6, 7, 8, 9, 10, 11, 12, 13, 14, 15, 16, 17, 18, 19, 20, etc., as well as 1.1, 1.2, 1.3, 1.4, 1.5, etc., 2.1, 2.2, 2.3, 2.4, 2.5, etc., and so forth.

Reference to a series of ranges includes ranges which combine the values of the boundaries of different ranges within the series. Thus, to illustrate reference to a series of ranges of 2-72 hours, 2-48 hours, 4-24 hours, 4-18 hours and 6-12 hours, includes ranges of 2-6 hours, 2, 12 hours, 2-18 hours, 2-24 hours, etc., and 4-27 hours, 4-48 hours, 4-6 hours, etc.

As used herein, an exponent can be represented in various ways. For example, $4.5 \times 10^{11}$ can also be represented as 4.5 $e^{11}$, and $5.0 \times 10^{11}$ can be represented as 5e11.

The invention is generally disclosed herein using affirmative language to describe the numerous embodiments and aspects. The invention also specifically includes embodiments in which particular subject matter is excluded, in full or in part, such as substances or materials, method steps and conditions, protocols, or procedures. For example, in certain embodiments or aspects of the invention, materials and/or method steps are excluded. Thus, even though the invention is generally not expressed herein in terms of what the invention does not include aspects that are not expressly excluded in the invention are nevertheless disclosed herein.

A number of embodiments of the invention have been described. Nevertheless, one skilled in the art, without departing from the spirit and scope of the invention, can make various changes and modifications of the invention to adapt it to various usages and conditions. Accordingly, the following examples are intended to illustrate but not limit the scope of the invention claimed.

EXAMPLES

Example 1

This example includes a description of various materials and methods.

AAV vectors and empty capsids: AAV vectors were prepared as previously described (Matsushita T., et al., *Gene. Ther.* 5, 938-945 (1998)). Genome-containing vectors and empty AAV capsid particles were purified by cesium chloride gradient centrifugation (Ayuso E., et al., *Gene. Ther.* 17, 503-510 (2010)). The AAV vectors used in the in vivo experiments expressed human F.IX under the control of a liver-specific promoter (Manno C. S., et al., *Nat. Med.* 12, 342-347 (2006)).

Figure 13A:
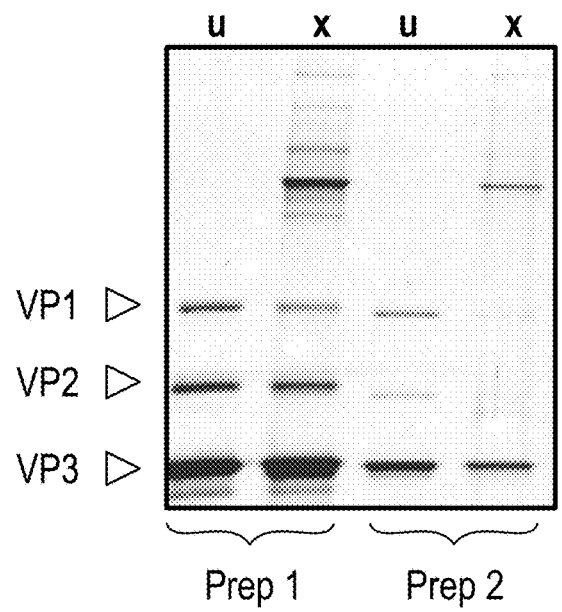
FIGS. 13A-13C show characterization of cross-linked AAV capsid preparations. (a) Denaturing SDS-PAGE followed by silver staining of AAV vectors untreated (u) or cross-linked (x) with formaldehyde, indicated are the capsid structural proteins VP-1, VP-2, and VP-3. Two vector preparations are shown, in both cases untreated vectors underwent the same exact cross-linking steps as the cross-linked vectors except for the addition of formaldehyde in the cross linking solution. For each preparation, approximately $1 \times 10^{10}$ cp were loaded onto the wells. (b) GFP expression in HEK293 cells transduced for 24 hours with untreated or cross-linked AAV2-GFP vectors at an MOI of $1 \times 10^4$. Shown are the % of GFP cells analyzed by flow cytometry. (c) Recognition of cross-linked capsid by the anti-AAV2 A20 antibody. To test whether cross-linked AAV2 capsid was recognized by the monoclonal antibody A20 ELISA plates were coated with a 1:500 dilution of the antibody in coating buffer. After blocking, various amounts (x-axis) of untreated AAV2, cross-linked AAV2, or AAV8 (negative control) were loaded on the plate. Binding of the virus was verified by adding a 1:500 dilution of IVIg, followed by an anti-human IgG H+L chain antibody horseradish peroxydase-conjugated (1:1000, Caltag). Results are reported as optical density (OD) reading at 450 nm (y-axis).
Figure 13B:
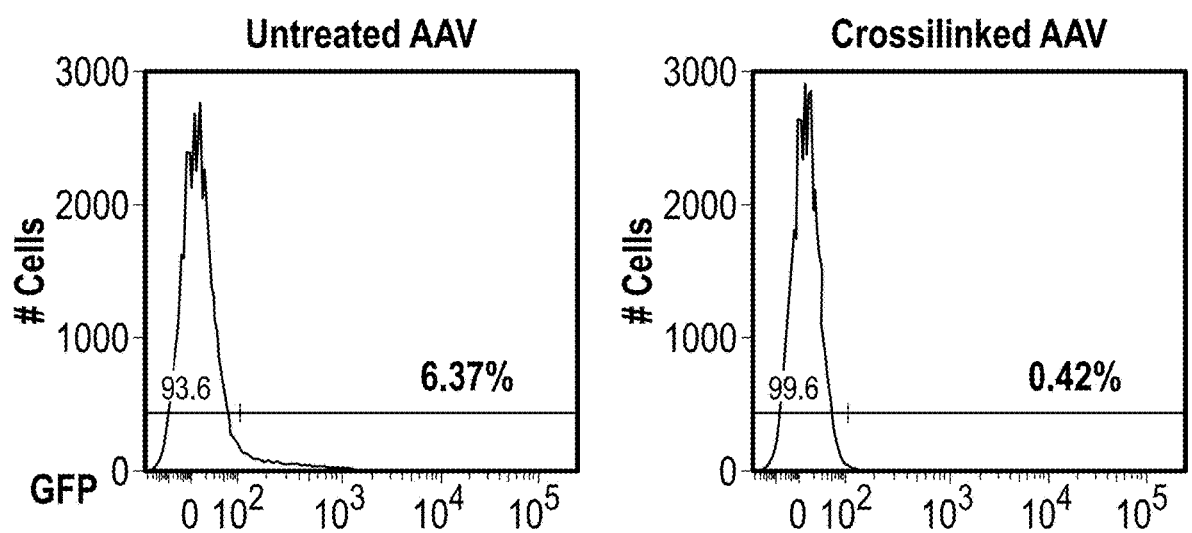
Figure 13C:
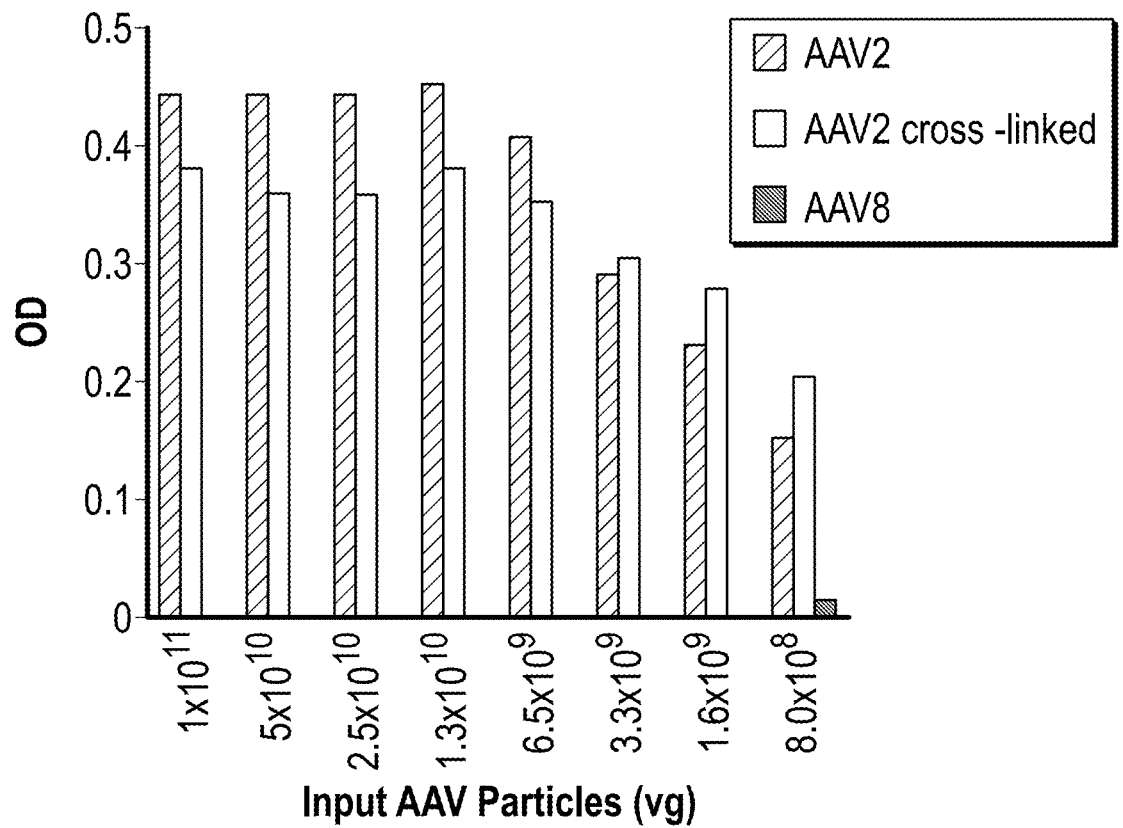
Figure 14:
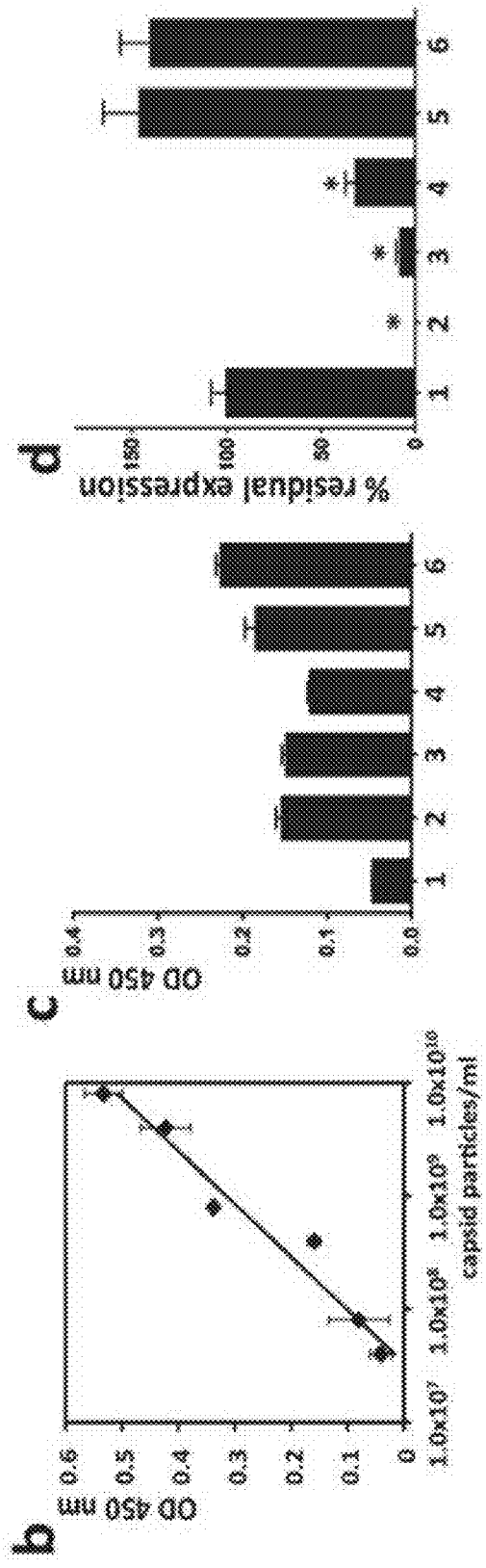
FIGS. 14A-14D show a probable mechanism of action of AAV empty capsids. Mice passively immunized with IVIg received AAV8-F.IX vector alone or formulated with increasing amounts of empty AAV capsids (a). IgG:capsid complexes in plasma was assayed. As standard curve in the assay, known quantities of AAV8 capsid incubated with IVIg were used (b). Following vector administration, no immune complexes were detectable in the plasma of mice not pre-immunized with IVIg (c, column 1). IgG:capsid complexes were detectable in increasing amounts in IVIg-injected animals receiving vector only or vector and empty capsids (c, columns 2-6). Absorption of anti-capsid antibodies by empty AAV capsid resulted in a dose-dependent drop in anti-AAV8 NAb titer in mice (a) and, additionally, increasing levels of hF.IX transgene expression (d).
Figure 15:
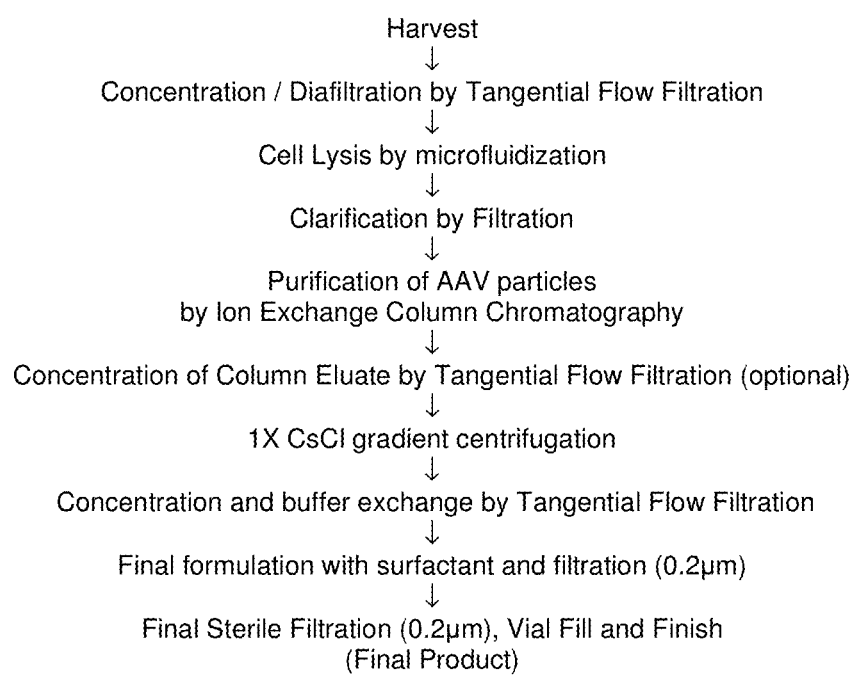
FIG. 15 shows a flow chart of suitable purification steps.

Cross-Linking: AAV capsids were cross-linked with two distinct protocols. In one protocol, $1 \times 10^{13}$ AAV particles per milliliter were incubated with a 1:200 dilution of 37% formaldehyde (Sigma) for 3 weeks at 4° C. on a rotating wheel. Formaldehyde in the samples was then neutralized by adding 3.75% (w/v) sodium metabisulfite (1:100). Vector was dialyzed in 1×PBS, filtered, and stored at −80° C. Untreated vectors were processed identically but in the absence of formaldehyde. In the second protocol, vector was incubated with 5 mM 3,3'-Dithiobis[sulfosuccinimidylpropionate] (DTSSP, Pierce-Thermo Scientific). Cross-linking with DTSSP was carried on for 2 hours on ice. After cross-linking, vector was dialyzed in 1×PBS and stored at −80° C. Cross-linking did not affect capsid recognition by the anti-AAV2 monoclonal antibody A20 (FIG. 13).

Human Serum and Cell Samples: All human samples used in the study were collected under protocols approved by the Children's Hospital of Philadelphia and the University of Pittsburgh's Institutional Review Boards (IRB). Samples from pediatric subjects were acquired from a commercial source (Bioreclamation). De-identified peripheral blood mononuclear cell (PBMC) samples used for the preparation of dendritic cells (DC) (Mingozzi F., et al., *Nat. Med.* 13, 419-422 (2007)) were obtained from the Center for AIDS Research at the University of Pennsylvania.

Animal Studies: Animal studies were approved by the Institutional Animal Care and Use Committees (IACUC) at the Children's Hospital of Philadelphia and Charles River Laboratories Preclinical Services. Male C57BL/6 mice 8 to 10 weeks of age were purchased from Charles Rivers Laboratories. Intravenous immunoglobulin (IVIg, Gamunex) was injected intraperitoneally in a total volume of 200 µl of 1×PBS. For the non-human primate studies, vector was delivered by peripheral vein infusion as previously described (Nathwani A. C., et al., *Blood.* 109, 1414-1421 (2007)).

Antibody assays: in vitro anti-AAV neutralizing antibody assay was based on a previously described protocol (Mann, C. S. et al. *Nat Med* 12, 342-347 (2006)) modified by using an AAV vector expressing reporter gene luciferase to increase the sensitivity of the assay. In the assay, the NAb titer corresponds to the reciprocal dilution of the test serum at which 50% inhibition of the luciferase signal is observed compared to the signal of the "virus only" control. The percent inhibition of the reporter signal at a 1:1 dilution of test serum represents the inhibitory activity of an undiluted test sample.

For the dot blot assay to detect anti-AAV antibodies, 1 µg of AAV2 or AAV8 capsids were spotted onto nitrocellulose membranes using a Minifold I Dot-Blot System (GE Healthcare Life Sciences). Membranes were then blocked overnight with TBS Western Blocking Reagent (Roche) and incubated with a 1:500 dilution of test sera for 1 hour at room temperature. Strips were washed with TBS with 0.1% Tween-20 (Bio-Rad) and bound IgG detected with a goat anti-human IgG antibody (Southern Biotech) labeled with IRDye 800 CW (LI-COR Biosciences). Blots were acquired with the Odyssey Infrared Imaging system (LI-COR Biosciences) at a resolution of 169 µm. Image densitometry was performed using the ImageJ software version 1.45s (National Institute of Health) and the resulting mean intensities expressed as a percentage of positive control (FACT pooled human plasma, George King) after background subtraction. The dot blot assay is described in more detail, as follows:

Production of Capsid Mutant: The AAV2 wild type capsid protein was mutagenized using the Quickchange kit (Invitrogen). Two mutations were inserted, resulting in two amino acid changes: R585A and R588A (the mutant capsid is indicated as $AAV_{585/8}$ in this document). The capsid was used to prepare the following material: $AAV_{585/8}$-GFP vector for in vitro transduction efficiency studies; $AAV_{585/8}$-FIX19 vector to study the ability of the mutant capsid to transduce liver and express human factor IX of mice; and $AAV_{585/8}$ empty capsids to study the ability of this mutant to act as a decoy for anti-AAV antibodies.

Reagents and Equipment:
Tris Buffered Saline, TBS, 10×, Sigma T5912 or equivalent
Western Blot Blocking Reagent, Roche Applied Bioscience 11921673001 or equivalent
Tween 20, Bio Rad 170-6531 or equivalent
Nitrocellulose Membranes, pore size 0.2 μm, Protran BA83-10402488
Gel Blot Paper GB003 (15×15 cm) Whatman®
Density-gradient purified AAV empty capsid,
Anti Human IgG Purified (UNLB), Southern Biotech 2040-01
928-38040 IRDye 800CW Protein Labeling Kit—High Molecular Weight
Control FACT plasma, George King Biomedical Cat #0020-1, Lot number D9d1 if available
Pool pediatric serum
4 well Dish Non Treated with lid, Thermo Scientific Cat #267061 or equivalent
Serological Pipettes, 5, 10, 25 mL
50 mL centrifuge/conical tubes, Corning 430290
Reagent reservoirs, Costar 4870
12-channel Multi-channel Pipettor 20-200 μL
P-20, P-200 and P-1000 Rainin Pipetman
Pipet Tips
Nunc-Immuno™ Tubes MiniSorp 4 ml, Polyethylene, 466982
12-channel reservoirs, Costar 4877
Vortex mixer
Tweezers
Aluminum foil
Odyssey Software (Li-Cor Biosciences)
ImageJ Software
Microsoft Excel
Equipment
Biological Safety Cabinet
Freezer, −80° C.
Refrigerator, 2-8° C.
Vacuum source
Odissey Infrared Imaging System (Li-Cor Biosciences)
Orbital Shaker
Preparation of Reagents
AAV empty capsid at a concentration $\geq 1 \times 10^{13}$ vg/mL
Store 100 μL aliquots at −80° C.
Blocking Buffer: Dilute Blocking Buffer 1:10 in 1×TBS. Prepare 70 mL of Blocking Buffer per plate and store at −20° C. for up to 4 months.
Dilution Buffer: dilute Blocking Buffer 1:1 in 1×TBS.
Washing Buffer: Prepare a solution of 1×TBS 0.1% (v/v) Tween 20. Store at 2-8° C. for up to one month.
Control Plasma FACT: Heat-inactivate the control plasma at 56° C. for 30 minutes and store 50 μL aliquots at −80° C. Assign an expiration date of 3 years from the date of manufacture. Do not refreeze thawed aliquots
Test Sample: Heat-inactivate the test serum or plasma sample at 56° C. for 30 minutes and store aliquots at −80° C.
Anti Human IgG CW800 labeled: Label Antibody according to manufacturer instructions. Final Antibody concentration should be 2 mg/ml and Dye/protein ratio between 1.5 to 2.

Procedure
Preparation of the Reagents: Day 1 of the Assay
Dilute AAV Empty capsid in TBS 1× to a final concentration of 10 μg/ml in a MiniSorp tube, 5 ml per plate.
Dilute Blocking Buffer in TBS 1×1/1000 in a MiniSorp tube, 5 ml per plate.
Place the nitrocellulose membrane and gel blot paper in a container allowing them to soak for 5 min in 1×TBS.
Plug Minifold System I to a vacuum source, place the filter support plate on top of the vacuum plenum, aligning the registration pins. Place the paper on the filter support plate, align the cut corners with the registration pins, repeat this procedure to place the nitrocellulose membrane on top of the gel blot paper.
Apply vacuum and spot 100 μl/well on the nitrocellulose membrane with a multichannel pipette according to this template (BB, Blocking Buffer; AAV, empty capsids):

|   | 1 | 2 | 3 | 4 | 5 | 6 | 7 | 8 | 9 | 10 | 11 | 12 |
|---|---|---|---|---|---|---|---|---|---|----|----|----|
| A | BB | AAV | BB | BB | BB | BB | BB | BB | BB | BB | AAV | BB |
| B | BB | AAV | AAV | AAV | AAV | AAV | AAV | AAV | AAV | AAV | AAV | BB |
| C | BB | AAV | AAV | AAV | AAV | AAV | AAV | AAV | AAV | AAV | AAV | BB |
| D | BB | AAV | BB | BB | BB | BB | BB | BB | BB | BB | AAV | BB |
| E | BB | AAV | BB | BB | BB | BB | BB | BB | BB | BB | AAV | BB |
| F | BB | AAV | AAV | AAV | AAV | AAV | AAV | AAV | AAV | AAV | AAV | BB |
| G | BB | AAV | AAV | AAV | AAV | AAV | AAV | AAV | AAV | AAV | AAV | BB |
| H | BB | AAV | BB | BB | BB | BB | BB | BB | BB | BB | AAV | BB |

With the vacuum still on, disassemble the manifold by unclamping, and use forceps to carefully remove the membrane. Allow the membrane to dry and block with 50 ml Blocking Buffer overnight at 4° C. on a shaker (200 rpm).
Sample Preparation and Incubation: Day 2
Prepare 2 mL of a 1:500 dilution of the test samples and controls (FACT plasma as positive and negative pediatric sample) using Diluent Buffer.
Cut the membrane into rectangles using forceps and scissors so that each piece will have two AAV and two BB spots.
Incubate membranes for 1 h at room temperature with samples and controls, on a shaker.
Wash 3× with washing buffer (10 ml, 5 minutes per wash).
Prepare a 1/10000 dilution of Anti Human IgG 800CW, using Dilution Buffer as diluent (2 ml per sample, 50 ml per plate).
Incubate samples for 1 h at room temperature covering the membranes with aluminum foil.
Wash 3× with washing buffer (10 ml, 5 minutes per wash), in the dark.
Place each membrane between 2 sheets of gel blot paper using tweezers. Let it dry and wrap with aluminum foil.
Image Acquisition: Open the Odyssey Software and open a new project
Place dry membranes face down on the Odyssey scanner
Determine acquisition area using the ruler on the scanner surface, and set the parameters on the dialogue panel:
  (1) Resolution: 169 μm
  (2) Focus: Membrane
  (3) Channel: 800
  (4) Intensity: 5
Save acquisition and export Image as colorized TIFF
Image J analysis
Open Tiff image with Image J software and split color channels (Image>Color>Split Channel), Draw a 25×25 oval selection using Specify Selection Tool (Edit>Selection>Specify)
Measure Mean Intensities for each AAV and BB spot, including FACT and Negative controls
Average the reading of each duplicate
Copy results to the assay report form, use formula at the bottom of the report form to calculate "percent of max" Mean Intensities.

% of Max Mean Intensity Formula

[(Mean intensity Unknown sample)−(Mean intensity Negative)]

[(Mean intensity Positive)−(Mean intensity Negative)]

Factor IX and Anti-Human F.IX Antibody Determination: Levels of human F.IX transgene product in mouse plasma were detected with a commercial ELISA kit from Affinity Biologicals. Human F.IX and anti-human F.IX antibodies in rhesus macaque plasma were determined as previously described (Mingozzi F. et al., *Blood.* 110, 2334-2341 (2007)).

AAV Vector Genome Copy Determination: Real time quantitative PCR (Q-PCR) primers and probes were as follows: for the detection of the AAV-F.IX vector genomes, forward primer 5'-CGAATTCTAGTCGTCGACCACTT-3', reverse primer 5'-CATGTTCACGCGCTGCATA-3', probe 5'-CACAATCTGCTAGCAAAG-3'. For the detection of the AAV-GFP vector genomes, forward primer 5'-AAGCTGACCCTGAAGTTCATC-3', reverse primer 5'-CTGCTTCATGTGGTCGGG-3', probe 5'-AAGCACTGCANCGCCGTAGGTA-3'. The assay was performed as previously described (Mingozzi F. et al., *Blood.* 110, 2334-2341 (2007)).

Intracellular Imaging and Cytotoxic T Lymphocyte (CTL) Assay: Image acquisition was performed with an Amnis ImageStreamX instrument (Amnis Corporation). Imaging was performed at a 40× magnification. At least 5000 cells were acquired for each condition. Cells were incubated with untreated or cross-linked AAV2 virus in serum-free medium. After one or four hours, cells were washed twice with 1×PBS and stained. For intracellular staining, $5×10^5$ cells were fixed and permeabilized for 20 min at 4° C. then washed with 1× Perm/Wash buffer (BD Bioscience). Cells were then stained with the anti-AAV antibody A20 (Fitzgerald Industries International) together with a rabbit anti-CD71 antibody (Epitomics) or DRAQ5 (Invitrogen). After 30 minutes at room temperature, cells were washed and stained with secondary antibodies. The CTL assay was previously described (Pien G. C., et al., *J. Clin. Invest.* 119, 1688-1695 (2009); (Mingozzi F. et al., *Blood.* 110, 2334-2341 (2007)).

Statistical Analysis: Statistical analysis was performed with GraphPad Prism version 5.0b (Graph Pad Software, Inc). p values <0.05 were considered significant.

Example 2

This example includes a description of observations and analysis of patients treated with Factor IX gene therapy and the discovery that there was substantial variation in anti-AAV antibody titers despite the selection of subjects based upon low AAV antibody titer.

Subjects enrolled in the AAV2-F.IX liver study (Manno, C. S. et al. *Nat Med* 12, 342-347 (2006)) and AAV8-F.IX liver study (Nathwani, A. C. et al., *New Engl. J. of Med.* 365, 2357-2365 (2011)) had detectable levels of anti-AAV antibodies (FIG. 16; Manno, C. S. et al. *Nat Med* 12, 342-347 (2006); and Nathwani, A. C. et al., *New Engl. J. of Med.* 365, 2357-2365 (2011)). Subjects in both studies received similar vector doses; however, while in the AAV2 study none of the subjects in the low- ($8×10^{10}$ vector genomes (vg)/kg) and mid- ($4×10^{11}$ vg/kg) dose cohorts exhibited detectable levels of transgene expression (Manno, C. S. et al. *Nat Med* 12, 342-347 (2006)), subjects in the AAV8 trial had detectable levels of clotting factor (>1%) in both low- ($2×10^{11}$ vg/kg) and mid ($6×10^{11}$ vg/kg) dose cohorts (Nathwani, A. C. et al., *New Engl. J. of Med.* 365, 2357-2365 (2011)). Possible explanations for the different outcome of these studies could be the higher tropism of AAV8 vectors for hepatocytes compared with AAV2 vectors (Gao, G. P. et al. *Proc Nail Acad Sci USA* 99, 11854-11859 (2002)) or the fact that the AAV8 vector carried a self-complementary genome, known to drive higher transgene expression levels. Published studies in non-human primates showed roughly equivalent levels of F.IX transgene expression following the delivery of AAV8 or AAV2 vectors carrying the same transgene expression cassette (Jiang, H. et al. *Blood* 108, 3321-3328 (2006); Mingozzi, F. et al. *Blood* 110, 2334-2341 (2007)). In both the AAV2 and AAV8 trials, subjects injected at the highest vector dose ($2×10^{12}$ vg/kg) had similar peak F.IX transgene product plasma levels (Manno, C. S. et al. *Nat Med* 12, 342-347 (2006); Nathwani, A. C. et al., *New Engl. J. of Med.* 365, 2357-2365 (2011)).

To evaluate individuals more rigorously, a series of sera from hemophilia subjects using a previously described in vitro NAb assay were screened (Manno, C. S. et al. *Nat Med* 12, 342-347 (2006)). Among those samples with a low NAb titer (from 1 to 3), a broad range of neutralizing activity in undiluted serum was measured (FIG. 16). The samples were then analyzed using a highly sensitive (FIG. 10) serotype-specific dot blot assay for total anti-AAV8 antibodies (FIG. 16).

Despite the pre-selection of subjects with low NAb titer, the dot blot analysis showed a marked variation in the amounts of total anti-AAV antibodies (both neutralizing and non-neutralizing) detected, with most of the adult subjects testing positive compared to pediatric subjects who were negative (FIG. 16).

These results indicate that adult human subjects who appear to have low-titer neutralizing antibodies (NAb) to AAV carry significant amounts of anti-AAV IgG not reliably detected by routine assays for NAb.

Example 3

This example includes a description of animal studies demonstrating that formulating or delivering AAV vectors with an excess of AAV empty capsids, even in animals with high titers of AAV Nabs, resulted in rescue of transduction in vivo after AAV vector delivery even in the presence of anti-AAV antibodies.

To study the effect of empty capsids on the efficiency of transduction of AAV vectors in vivo empty capsids were formulated with AAV vectors. First, in vitro studies revealed that inclusion of empty capsids in AAV vector preparations greatly reduced neutralizing activity of human serum in vitro (FIG. 11).

Second, to study the effect of empty capsids on the efficiency of transduction of AAV vectors in vivo, a mouse a mouse model of anti-AAV antibody responses (Scallan C. D., et al., *Blood.* 107, 1810-1817 (2006)) (FIG. 1a) was generated. An AAV8 vector expressing human F.IX (AAV8- hF.IX) was injected into naïve mice or mice that were immunized with a low dose of IVIg (0.5 mg/mouse), sufficient to result in an anti-AAV8 NAb titer ranging from 1 to 3 (FIGS. 1a,b). Vector doses of 1×10$^9$ and 5×10$^9$ vg/mouse, or the same vector doses formulated in ten-fold (10×) excess AAV8 empty capsids gave rise to similar levels of hF.IX in plasma in naïve animals IVIg immunization effectively blocked most liver transduction by vectors formulated in PBS, while formulation of vectors in 10× empty capsids rescued transgene expression (FIG. 1b). Vector gene copy number measured in livers collected from animals receiving 5×10$^9$ vg of AAV8-hF.IX confirmed these findings (FIG. 1c).

To confirm the findings, a similar study in rhesus macaques, which are natural hosts for AAV8 (Gao G. P., et al., *Proc. Natl. Acad. Sci. USA* 99, 11854-11859 (2002)), was performed. 30 animals were screened to identify a total of 7 monkeys with a NAb titer of 1. Similar to humans, despite the low NAb titer, baseline undiluted sera of the selected animals had a neutralizing activity in vitro from 10 to 80% and varying amounts of anti-AAV8 IgG in the dot blot assay (FIG. 17). At a dose of 1×10$^{12}$ vg/kg of AAV8-hF.IX, of the two animals that received vector alone, one (1001) expressed the hF.IX transgene only transiently due to the development of an anti-hF.IX antibody, a finding previously reported in rhesus macaques (Mingozzi F., et al., *Blood.* 110, 2334-2341 (2007); Nathwani A. C., et al., *Blood.* 107, 2653-2661 (2006); Nathwani A. C., et al., *Mol. Ther.* 19, 876-885 (2011)); the other animal, 1002, reached plateau hF.IX plasma levels of 67 ng/ml. In contrast, the animal injected with vector formulated in 9× empty AAV8 capsids, 2001, reached plateau levels of transgene expression almost 6-fold higher (FIG. 1d and FIG. 17). Animals 1002 and 2001 exhibited a similar anti-AAV8 neutralizing activity at baseline (~30%, FIG. 17).

Developed an anti-human F.IX inhibitory antibody. Dose escalation to 2×10$^{12}$ vg/kg led to similar results. One of the two animals dosed with vector only, 3001, did not achieve detectable levels of circulating hF.IX transgene product. The animal did not develop anti-hF.IX antibodies, and AAV vector genome copy number in liver (FIG. 18) suggesting that the 57% neutralizing activity of undiluted serum at baseline completely blocked vector transduction. The other animal dosed with vector only, 3002, reached plateau levels of circulating hF.IX of ~169 ng/ml. Of the two animals dosed with vector formulated in 9× empty capsids, 4001 (baseline neutralizing activity of 80%) showed ~415 ng/ml of hF.IX transgene product in plasma. 4002, with a serum baseline neutralizing activity of 55%, almost identical to 3001, had plateau hF.IX expression of 915 ng/ml (FIG. 1d and FIG. 17). Inclusion of empty capsids in the formulation did not affect AAV vector biodistribution (FIG. 18).

These results confirm, in a large animal model, findings in vitro and in vivo in mice on the enhancing effect that empty capsids have on AAV vector transduction efficiency following gene transfer through the intravascular space. Administration or co-formulation of AAV vectors with AAV empty capsids allows efficient transgene transduction of the target cells and expression even in the presence of anti-AAV NAb.

In the next studies, mice immunized with IVIg (FIG. 1a) that produced low and high titers of AAV antibodies were analyzed for AAV vector gene transduction in combination with increasing amounts of empty capsids. In brief, mice received 5×10$^9$ vg/mouse of vector alone or formulated in increasing amounts of empty AAV8 capsids (FIGS. 2a-d). In the presence of low-titer anti-AAV8 NAb titers (FIG. 2a), formulation of vector in a 10-fold excess of empty capsids completely rescued AAV vector transduction. An empty capsid excess of up to 100× the AAV8-F.IX dose did not inhibit AAV vector transduction. A 1000-fold excess of empty capsids resulted in a ~40% loss of transgene expression.

Figure 2:
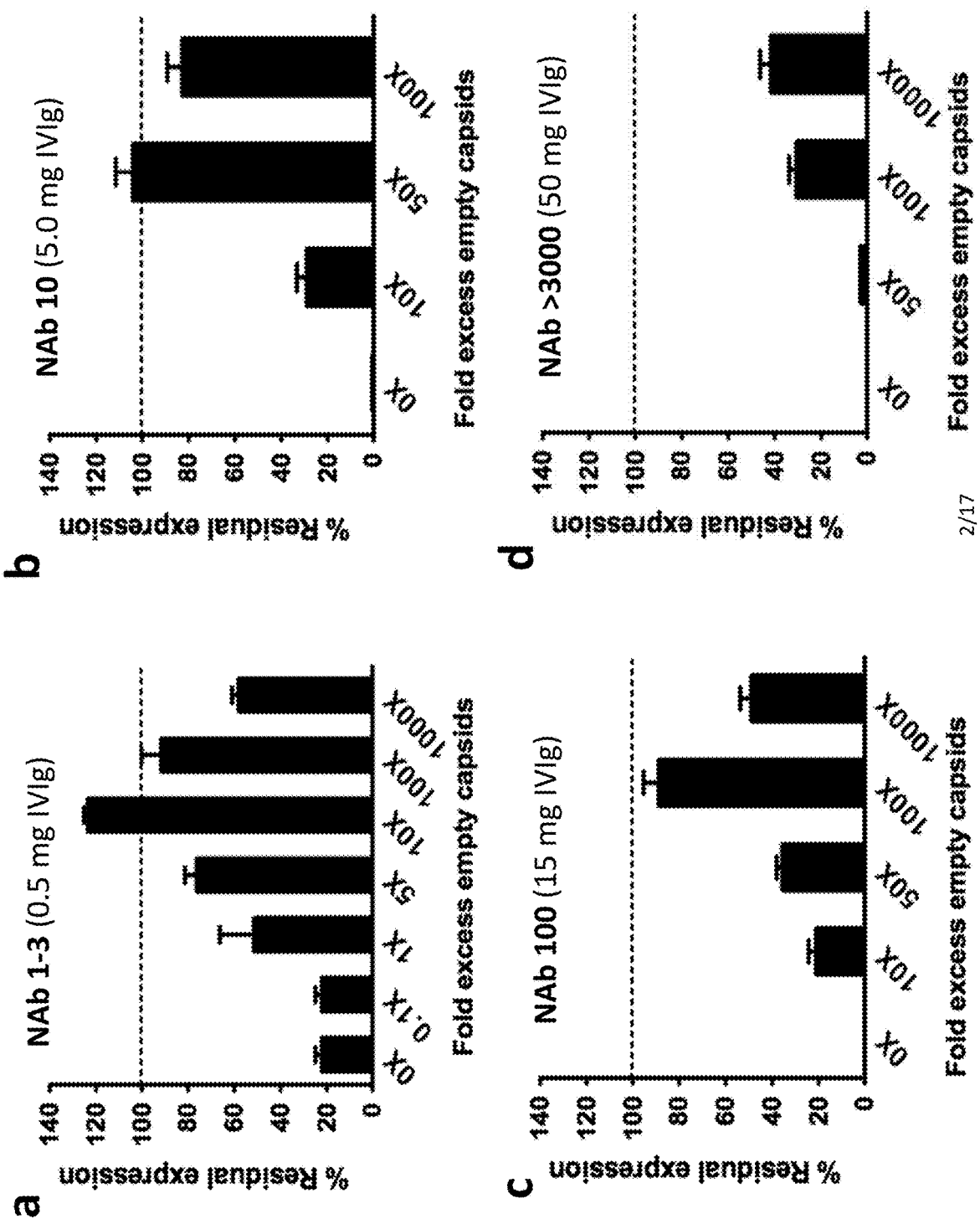
FIGS. 2A-2D show data indicating that addition of empty capsid in defined amounts based on pre-treatment NAb titers can overcome gene transduction barrier posed by anti-AAV antibodies. (a-d) % residual F.IX transgene expression in mice immunized with 0.5 mg (a), 5.0 mg (b), 15 mg (c), or 50 mg (d) IVIg and injected 24 hours later with $5\times10^9$ vg/mouse of AAV8-F.IX vector alone (dose) or vector formulated in excess empty capsids as indicated in the y-axes. The % residual expression is calculated relative to the F.IX transgene product plasma levels in naïve animals receiving the AAV-F.IX vector alone. Results are shown as average of residual expression (n=5 animals per group); error bars represent the standard error of the mean.

Similarly, full rescue of liver transduction was obtained with an excess of 50× and 100× empty capsids in the presence of NAb titers of 10 and 100, respectively (FIGS. 2b,c). However, full rescue of liver gene transduction in the presence of extremely high NAb titers (>3000), even by adding a 1000× excess of empty capsids (FIG. 2d), was not detected.

Figure 12:
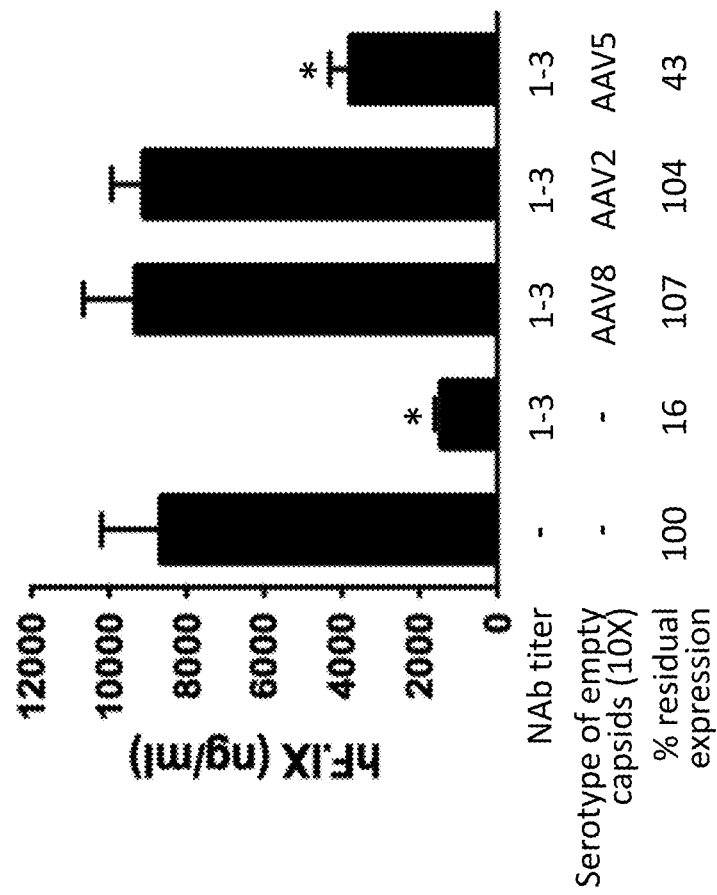
FIG. 12 shows that empty capsids from alternate (non-identical) AAV serotypes protect AAV8-F.IX from NAb neutralization. Male C57BL/6 mice (n=5 per group) were passively immunized with 0.5 mg of IVIg (1:1) or injected with PBS (−) intraperitoneally. 24 hours after, animals received $5 \times 10^9$ vg of an AAV8-F.IX vector alone (−) or formulated with a 10× excess of AAV8, AAV2, or AAV5 empty capsids. Results are shown as average, error bars represent the standard deviation of the mean. The % residual expression is calculated relative to the F.IX transgene product levels in naïve animals receiving the AAV-F.IX vector alone. *, p<0.05 vs. vector alone in naïve animals.

Due to apparent cross-reactivity of anti-AAV Nab (Boutin S., et al., *Hum. Gene. Ther.* 21, 704-712 (2010); Calcedo R., et al., *J. Infect. Dis.* 199, 381-390 (2009)), AAV8-F.IX vector transduction in the presence of anti-AAV8 NAb was equally rescued by AAV8 or AAV2 empty capsids, while AAV5 empty capsids were not as effective (FIG. 12). Thus, due to cross reactivity it is clear that empty capsids from one AAV serotype can be used to inhibit or reduce the affect of neutralizing antibodies against one or more different AAV vector serotypes (e.g., AAV8 vector in combination with AAV2 empty capsids, and vice versa).

These findings demonstrate that AAV empty capsids enhance liver transduction after systemic vector delivery in the presence of anti-AAV Nab, and in a dose-dependent fashion. Using excess empty capsid will overcome AAV vector neutralization in higher NAb titer animals to effect efficient transgene transduction in vivo. These results also demonstrate that cross-reactive empty capsid serotypes can be used in combination with different AAV vector serotypes to inhibit or reduce AAV vector neutralization.

Example 4

This example includes a description of animal studies demonstrating that cross-linked empty capsids reduce capsid immunogenicity while maintain functional inhibition of AAV vector neutralization by AAV antibodies.

Entry of empty capsids into a target cell would likely increase levels of MHC class I presentation of capsid epitopes (Mingozzi, F., et al., *Current Gene Therapy* 11, 321-330 (2011); Finn J. D., et al., *Mol. Ther.* 18, 135-142 (2010); Pien G. C., et al., *J. Clin. Invest.* 119, 1688-1695 (2009); Johnson J. S., et al., *J. Virol.* 83, 2632-2644 (2009)). To reduce their ability to enter a cell, without substantially compromising the ability to bind to or react with pre-existing anti-AAV antibodies, empty AAV capsids were cross-linked prior to adding them to the AAV-F.IX vector formulation. Results with the formaldehyde cross-linking method are represented; the DTSSP method for capsid cross-linking gave similar results.

Figure 3:
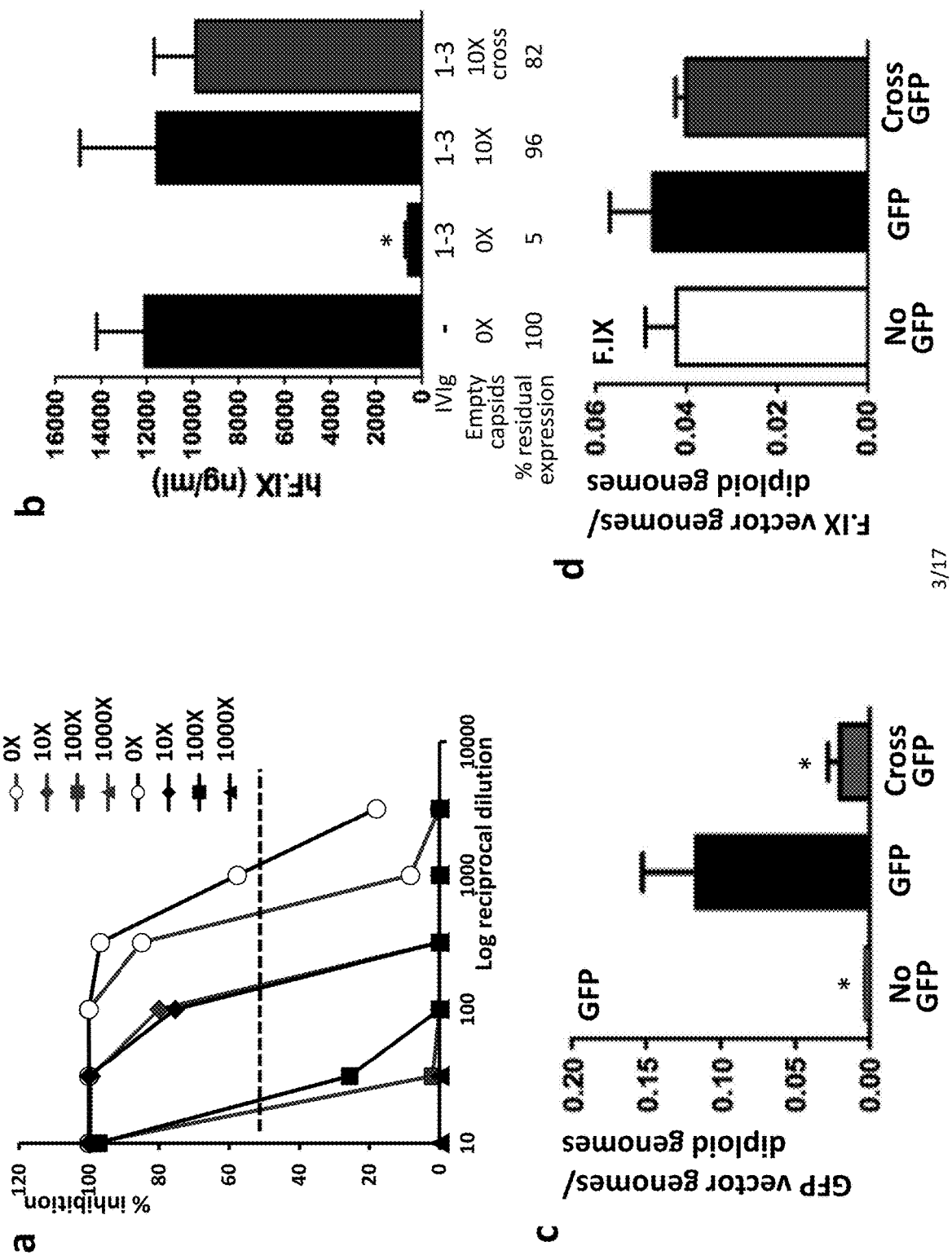
FIGS. 3A-3D show data indicating that cross-linked empty AAV capsids retain the ability to block NAb in vitro and in vivo. (a) An AAV8 vector expressing luciferase (AAV8-Luciferase, MOI $1\times10^3$) was incubated with half-log dilutions of IVIg alone (0×) or in the presence of excess untreated (black lines) or cross-linked (red lines) empty AAV8 capsids (10×, 100×, or 1000× the MOI). % inhibition was determined against the intensity of the reporter signal for AAV8-Luciferase vector not incubated with IVIg after background subtraction. (b) Male C57BL/6 mice (n=5 per group) were passively immunized with 0.5 mg of IVIg (resulting in an NAb titer of 1-3) or injected with PBS (−). 24 hours later, animals received $5\times10^9$ vg of an AAV8-F.IX vector alone (0×) or formulated with a 10× excess of untreated (black bar, 10×) or cross-linked (red bar, 10× Cross) AAV8 empty capsids. Results are shown as average, error bars represent the standard deviation of the mean. The % residual expression is calculated relative to the F.IX transgene product levels in naïve animals receiving the AAV-F.IX vector alone. *, $p<0.05$ vs. vector alone in naïve animals (c,d) Vector genome copy number in liver of mice 2 weeks post-gene transfer determined by Q-PCR (n=5/group). (c) AAV-GFP vector genome copy number per diploid genome. (d) AAV-F.IX vector genome copy number per diploid genome. All animals received $5\times10^9$ vg of an AAV8-F.IX vector either alone (white bars, No GFP), together with $5\times10^{10}$ vg of an untreated AAV8-GFP vector (black bars, GFP), or together with $5\times10^{10}$ vg of a cross-linked AAV8-GFP vector (red bars, Cross GFP). Results are expressed as average, error bars represent the standard deviation of the mean. *, $p<0.05$ vs. untreated GFP vector.

Cross-linking of AAV vectors was verified by SDS-PAGE and testing transduction efficiency in vitro (FIG. 13). Cross-linked empty AAV capsids retained their ability to adsorb anti-AAV NAb in vitro (FIG. 3a) and in vivo in mice (FIG. 3b).

Figure 4C:
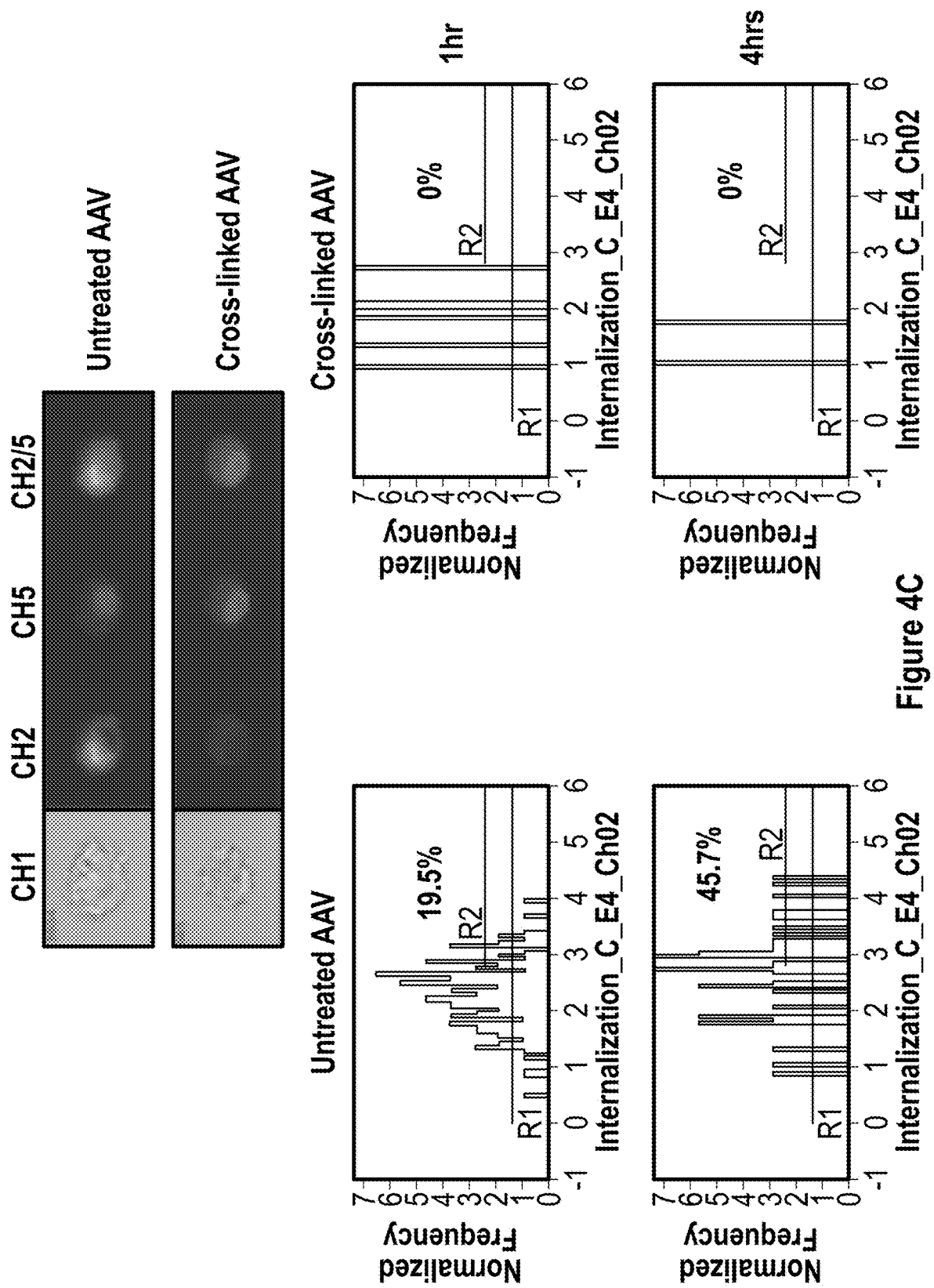
Figure 4D:
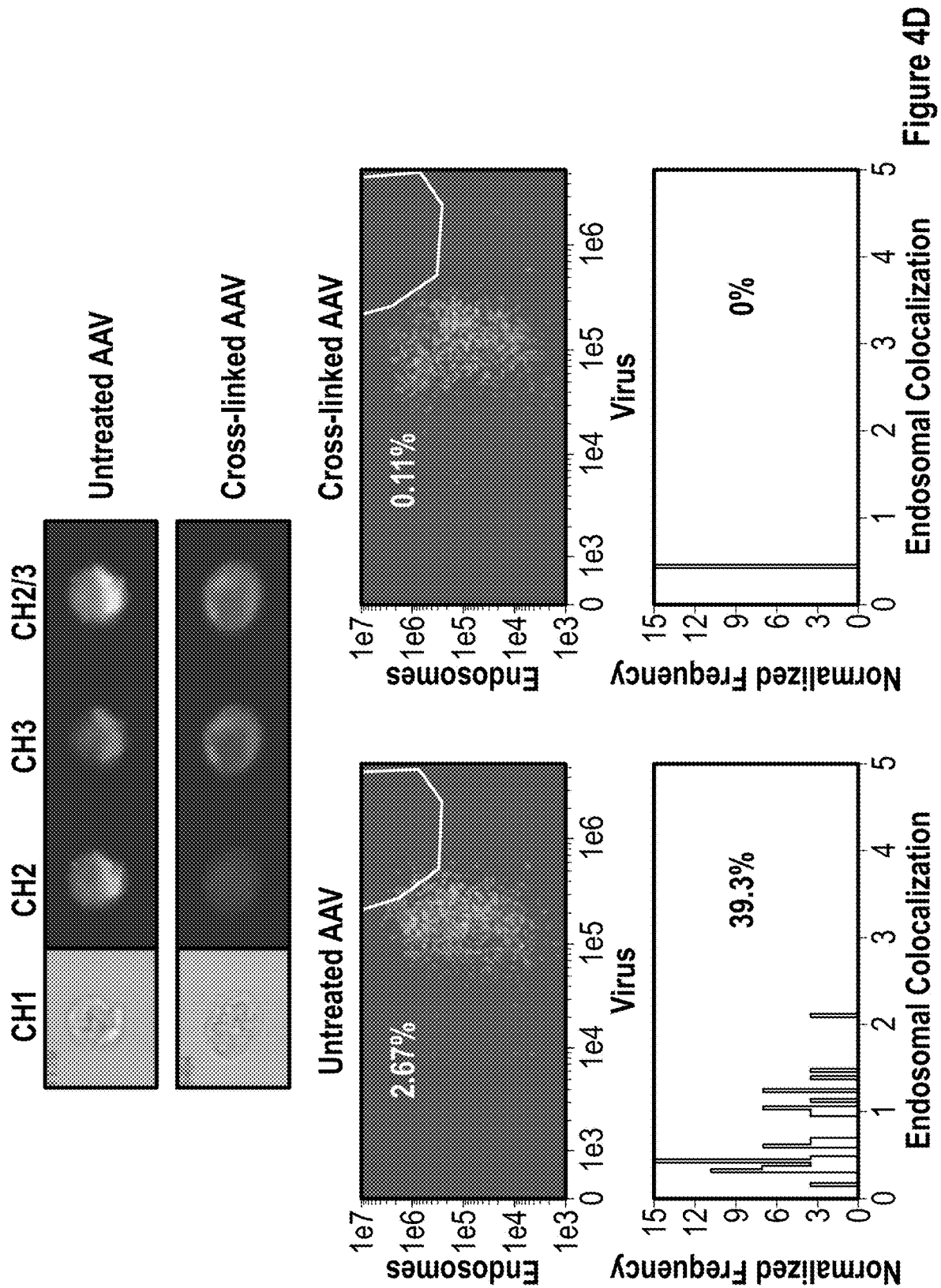
Figure 5:
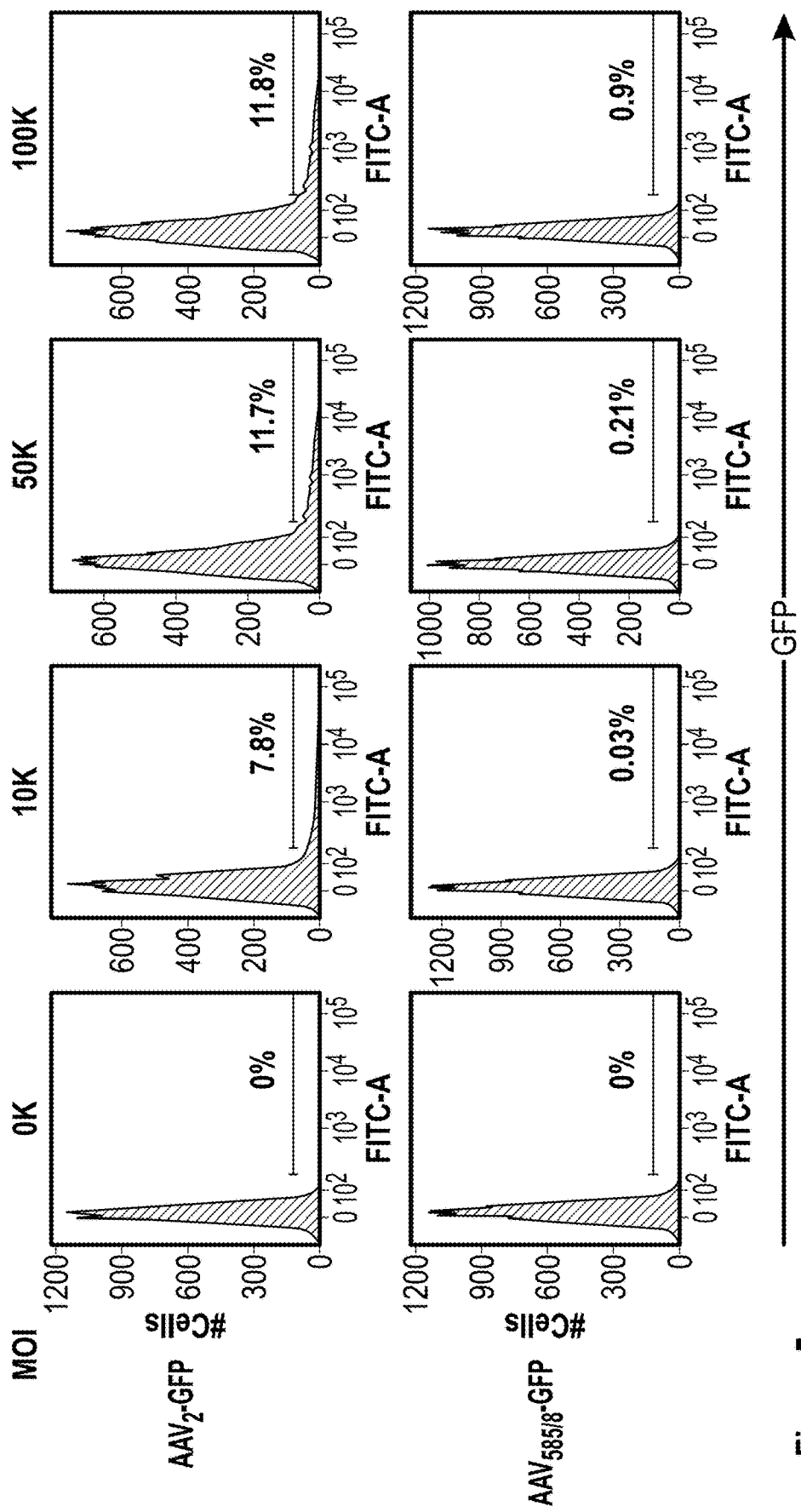
FIG. 5 shows data indicating that $AAV_{585/8}$ mutant (AAV2 capsid protein R585A and R588A double mutant) exhibited impaired ability to transduce cells in vitro compared to wild-type AAV2 ($AAV_2$). HEK293 cells were transduced overnight with AAV vectors expressing green fluorescent protein (GFP) at a multiplicity of infection (MOI) of 0 (0K, no virus control), 10000 (10K), 50000 (50K), or 100000 (100K). 24 hours later, cells were trypsinized and analyzed for GFP using a flow cytometer. % GFP positive cells for each condition are shown within the histogram plots. Compared to the $AAV_2$-GFP control, the $AAV_{585/8}$-GFP vector mutant showed markedly decreased transduction efficiency in vitro.
Figure 6:
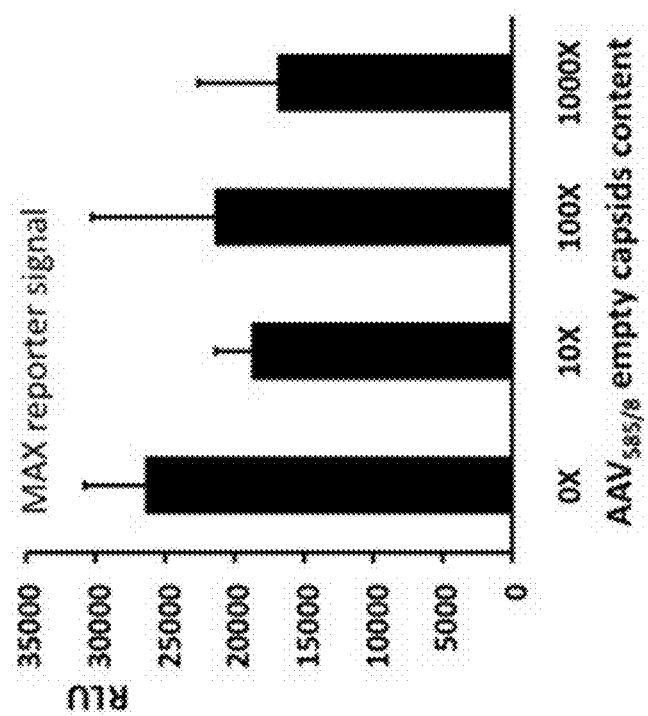
FIG. 6 shows data indicating that a large excess of $AAV_{585/8}$ empty capsids does not inhibit transduction of AAV8 vectors in vitro. HEK295 cells were transduced with an AAV8 vector expressing luciferase. The vector was mixed with variable amounts of $AAV_{585/8}$ empty capsids: 0-fold (0×, no empty capsid control), 10-fold (10×), 100-fold (100×), and 1000-fold (1000×) the amount of AAV8-Luciferase vector. Luciferase activity was measured 24 hours after transduction using a luminometer. Results are expressed as relative light units (RLU), bars represent average and standard deviation of triplicate testing. No significant inhibition of transduction was observed at any of the studied conditions.
Figure 7:
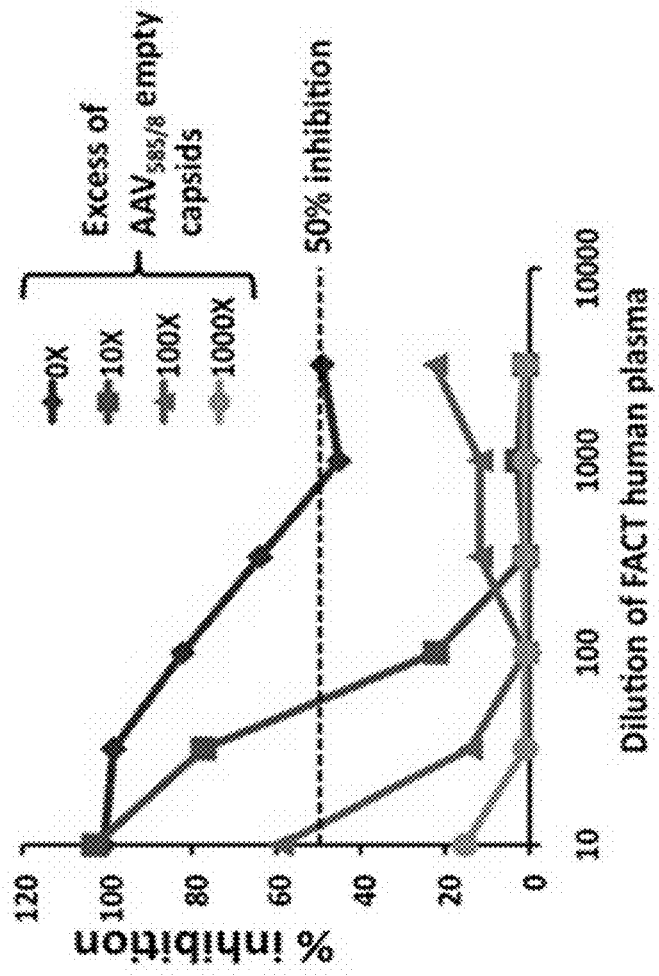
FIG. 7 shows data indicating that $AAV_{585/8}$ empty capsids protect AAV vectors from anti-AAV antibody-mediated neutralization in vitro. A reporter AAV8 vector expressing luciferase was incubated with increasing dilutions pooled normal plasma (FACT plasma, George King Bio) alone (0×) or in the presence of increasing amounts of $AAV_{585/8}$ empty capsids (10×, 100×, 1000× the amount of AAV8-Luciferase vector). After one hour incubation at 37° C., vectors were used to transduce HEK293 cells in vitro. Percent inhibition was measured relative to a control in which the reporter vector was incubated with medium only instead of pooled plasma. The addition of increasing amounts of $AAV_{585/8}$ empty capsids protects the AAV8-Luciferase vector from antibody-mediated neutralization.
Figure 8:
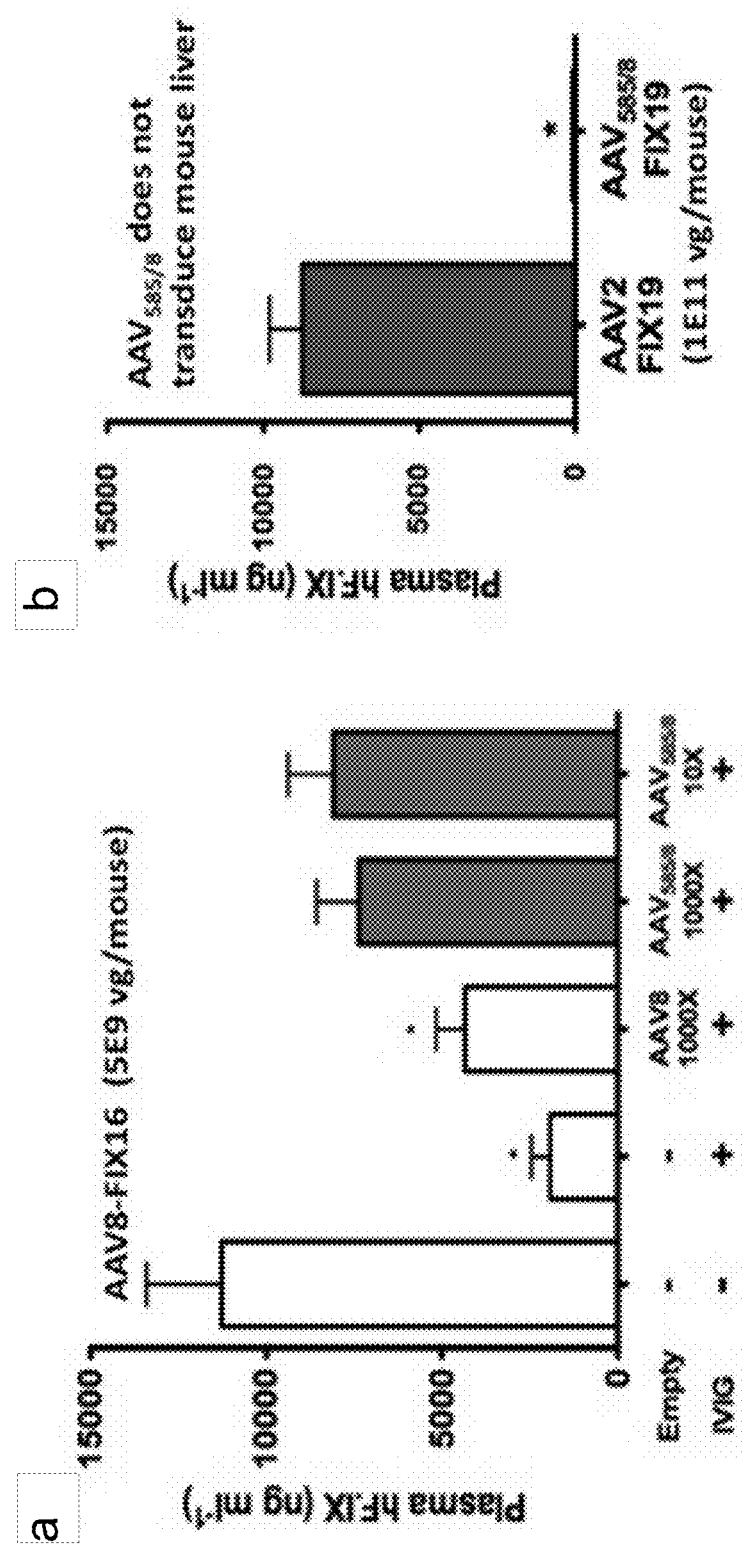
FIGS. 8A-8B show data indicating that $AAV_{585/8}$ empty capsids protect AAV vectors from anti-AAV antibody-mediated neutralization in vivo, while they do not transduce the liver efficiently. (a) C57BL/6 mice (n=4/5 per group) received an AAV8-FIX16 vector expressing coagulation factor IX (FIX) at a dose of 5E9 vg/mouse. All experimental groups except one (IVIG "−") received purified human IgG (IVIG) intraperitoneally 24 hours before vector injection (IVIG "+"). The AAV8-FIX16 vector was give alone (Empty "−"), mixed with a 1000-fold excess of AAV8 empty capsids (Empty "AAV8 1000×), mixed with a 1000-fold excess of $AAV_{585/8}$ empty capsids (Empty "$AAV_{585/8}$ 1000×), or mixed with a 10-fold excess of $AAV_{585/8}$ empty capsids (Empty "$AAV_{585/8}$ 10×). AAV8-FIX16 vector was efficiently neutralized by IVIG when given alone. $AAV_{585/8}$ empty capsids protected the AAV8-FIX16 vector from antibody-mediated neutralization at 10× and 1000× excess without inhibiting transduction efficiency. Conversely, 1000× excess AAV8 empty capsids resulted in inhibition of AAV8-FIX16 transduction, likely due to receptor binding competition. (b) C57BL/6 mice (n=4 per group) received AAV-FIX19 vectors expressing coagulation factor IX (FIX) at a dose of 1E11 vg/mouse. One group received an $AAV_2$-FIX19 vector, the other group the mutant $AAV_{585/8}$-FIX19 vector. The mutant vector does not transduce the mouse liver.
Figure 9:
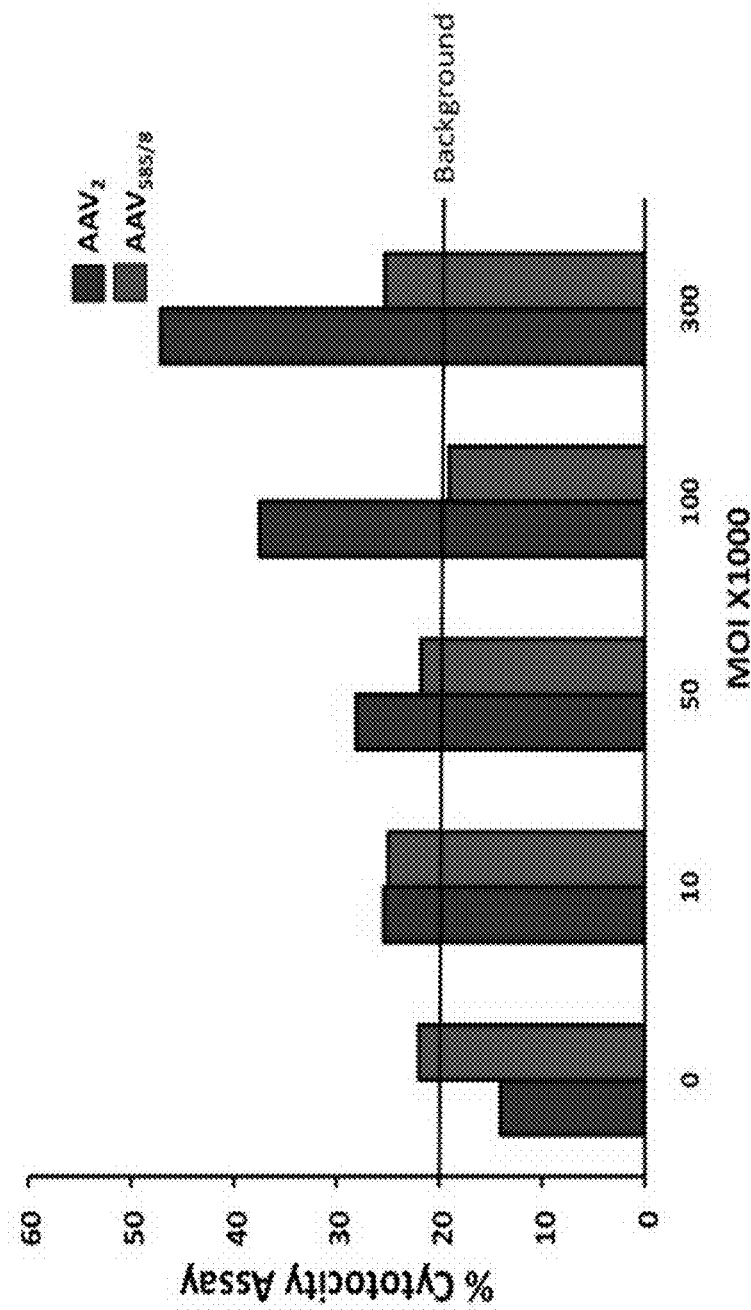
FIG. 9 shows data indicating that the $AAV_{585/5}$ capsid antigen is not efficiently presented on MHC class I. Human hepatocyte target cells transduced with increasing MOI of an AAV2 vector control or the $AAV_{585/8}$ vector were used as targets in a cytotoxic T lymphocytes (CTL) assay. HLA-matched CTLs were expanded in vitro against the AAV antigen and used in the assay as effector cells. No killing was observed with the $AAV_{585/8}$ mutant over a high range of MOIs. The horizontal line in the assay represents the background release of lactate dehydrogenase (used in the assay as a measure of CTL-mediated cell lysis) in cell culture medium.

To analyze liver tropism of cross-linked empty capsids in vivo, mice were administered an AAV-F.IX vector alone, or mixed with a 10× excess of an untreated or cross-linked AAV-GFP vector. Cross-linking significantly detargeted the AAV-GFP vector from liver (FIG. 3c), while AAV-F.IX vector genomes were detectable at similar levels in animals from all experimental groups (FIG. 3*d*). Cross-linking did not detectably alter AAV vector biodistribution in spleen or other lymphoid organs.

Flow imaging of human hepatocytes transduced in vitro with untreated or cross-linked empty AAV2 capsids showed that cross-linking blocked the entry of empty AAV capsids into the cell (FIG. 4a). Cross-linking was also associated with the inability of cross-linked AAV capsid to trigger killing of target human hepatocytes in vitro in a CTL assay (FIG. 4b) (Finn J. D., et al., *Mol. Ther.* 18, 135-142 (2010); Pien G. C., et al., *J. Clin. Invest.* 119, 1688-1695 (2009)). Finally, cross-linking of AAV capsid decreased both internalization (FIG. 4c) and endosomal localization (FIG. 4d) of capsid in vitro in monocyte-derived human DCs.

These results indicate that cross-linked AAV capsids retain the ability to enhance vector transduction in the presence of anti-AAV NAb. Furthermore, the studies indicate that cross-linking significantly decreases cellular uptake of AAV vectors, potentially reducing the risk of flagging transduced hepatocytes (and other AAV vector transduced cells) for immune-mediated destruction.

Example 5

This example includes a description of patient treatment studies employing AAV vectors and/or empty capsid AAV to treat a disease or disorder.

In patients affected by a metabolic or genetic disease requiring administration of AAV vectors the pre-existing NAb titer will be determined using an in vitro neutralization assay. Serial dilution of serum from the patient will be incubated at 37° C. with an AAV vector expressing a luciferase reporter. Increasing quantities of AAV empty capsids will be added to the reaction, from 1× to 10000×. The excess of empty AAV capsids that will result in a NAb titer of <1:1 can be used to produce a formulation with a AAV vector for transgene transfer. Thus, samples such as serum or plasma samples from candidate patients for gene therapy with AAV vectors will be analyzed for anti-AAV neutralizing antibodies using an AAV antibody (e.g., neutralizing antibody or "NAb") assay.

Briefly, the assay is performed by incubating a sample from a patient with an AAV vector expressing a reporter transgene (e.g., luciferase, GFP, CAT etc). The residual reporter gene expression measured in vitro after the neutralization of the AAV vector in the patient's serum or plasma will give the antibody titer, usually expressed as the serum/plasma dilution at which 50% inhibition of transduction is observed. For example, if a dilution of 1:10 of serum inhibits the activity of the AAV-reporter gene virus, then the anti-AAV NAb amount (titer) will be 1:10.

Based on the assay results that provide the AAV antibody amount (titer), subjects can optionally be classified in a manner similar to the following:

- Low titer (from undetectable to 1:3): these individuals will receive 1 to 10× excess empty AAV capsids with the AAV vector.
- Mid titer (from 1:3 to 1:100): these individuals will receive a 5 to 1000× excess empty AAV capsids with the AAV vector.
- High titer (above 1:100): these individuals will receive a 10 to 10000× excess empty AAV capsids with the AAV vector.

The quantity of empty capsids to be included in the preparations will be determined by performing the in vitro AAV antibody assay described herein in the presence of increasing amounts of empty AAV capsids. For example, if a patient has a NAb titer of 1:10, the serum/plasma will be incubated with 1×, 5×, 10×, 50×, 100×, 500×, 1000× (and also more refilled excess quantities) of empty capsids to determine the minimal amount of empty AAV capsids to be used for a pharmacological formulation of the AAV vector.

In a specific example of gene therapy, a hemophilia B patient is scheduled for gene transfer with an AAV-FIX vector. The patient has an anti-AAV neutralizing antibody titer of 1:10 as determined by an NAb assay. However, by adding 5× empty capsids titer falls to <1:1.

For this patient the AAV-FIX vector will be formulated with 5× cross-linked empty capsids in a pharmaceutically acceptable carrier. Assuming that the patient is scheduled to receive an AAV-FIX dose of $1\times10^{12}$ vg/kg, he will receive this dose formulated in $5\times10^{12}$ cp/kg of AAV empty capsids (optionally cross-linked). The AAV-FIX vector and AAV empty capsids will be manufactured using current Good Manufacturing Procedures, and subjected to appropriate quality control tests to ensure product purity, potency, safety and stability (Wright J. F., *Gene Ther.* 2008; 15:840-848). Measurement of the concentration of purified empty capsids to enable an accurate and reproducible admixture ratio with AAV vector in the final formulated product will be based on the extinction co-efficient of AAV capsid protein (Sommer J. M., et al., *Mol. Ther.* 2003; 7:122-128), or other known methods.

The empty capsids or viral genome containing capsids typically have a serotype that reacts with an antibody produced in a subject to be treated in accordance with the invention. For example, a subject that produces an antibody that reacts with or neutralizes AAV8 can be administered an AAV8 empty capsid or AAV8 viral genome containing capsid. The empty capsids or viral genome containing capsids added to the vector preparation can also be of another serotype due to cross-reactivity of antibodies that react with more than one serotype. For example, AAV2 empty capsids or AAV2 viral genome containing capsids added in a specific amount to an AAV8 vector expressing the transgene due to cross-reactivity of anti-AAV8 antibodies with AAV2.

Empty or viral genome containing capsids or capsid proteins can also comprise a mixture of two or more serotypes that react with antibodies produced in a subject. For example, a subject that produces antibodies that react with or neutralize AAV2 and AAV8 can be administered AAV2 and AAV8 empty capsids.

Example 6

This example includes a description of studies in which $AAV_{585/8}$ mutant capsid was able to adsorb anti-AAV antibodies but did not substantially transduce cells.

The studies were performed as described in the description for FIGS. 5 to 9. The studies show that $AAV_{585/8}$ mutant capsid inhibits or blocks antibody-mediated neutralization of an AAV8 vector in vitro and in vivo. The studies also show that the $AAV_{585/8}$ capsid can be used in large excess of the therapeutic AAV vector without interfering with the efficiency of vector transduction as the $AAV_{585/8}$ capsid does not compete for receptor binding.

Furthermore, the $AAV_{585/8}$ mutant capsid is derived from $AAV_2$, which is the most prevalent serotype of AAV in humans. Accordingly, AAV2 should adsorb the vast majority of circulating antibodies and provide protection of virtually all AAV serotypes from neutralization.

AAV2 mutant capsid may act as a universal solution to the problem of anti-AAV antibodies. The mutant capsid does not substantially infect cells in vitro and in vivo, and it does not seem to contribute to the overall antigen load of target cells, and therefore AAV2 mutant does not increase the extent of CTL-mediated lysis of AAV vector-transduced target cells.

Example 7

This example includes a description of studies showing a probable mechanism of action of AAV empty capsids.

Mice passively immunized with IVIg to an NAb titer >10 received an AAV8-F.IX (Factor IX) vector alone, or formulated with increasing amounts of AAV empty capsids (FIG. 14*a*). Plasma was collected one day post-vector delivery and assayed for IgG:capsid complexes. As standard curve in the assay, known quantities of AAV8 capsid incubated with IVIg were used (FIG. 14*b*). Following vector administration, no immune complexes were detectable in the plasma of mice that were not pre-immunized with IVIg (FIG. 14*c*, column 1). In contrast, IgG:capsid complexes were detectable in increasing amounts in IVIg-injected animals receiving vector only or vector and empty capsids (FIG. 14*c*, columns 2-6). Absorption of anti-AAV capsid antibodies by empty AAV capsid resulted in a dose-dependent drop in anti-AAV8 NAb titer in mice one day post vector delivery (FIG. 14*a*) and, ultimately, in increasing levels of hF.IX transgene expression (FIG. 14*d*). The foregoing studies demonstrate that empty AAV capsids act as a decoy and bind to anti-AAV antibodies, thereby protecting AAV vectors from antibody mediated neutralization.

REFERENCES

1. Mingozzi F, High K A. Therapeutic in vivo gene transfer for genetic disease using AAV: progress and challenges. Nat Rev Genet. 2011; 12:341-355.
2. High K A. AAV-mediated gene transfer for hemophilia. Ann N Y Acad Sci. 2001; 953: 64-74.
3. Basner-Tschakarjan E, Mingozzi F, Chen Y, et al. Dose-dependent activation of capsid-specific T cells after AAV serotype 8 vector administration in a clinical study for hemophilia. Mol Ther. 2011; in press.
4. Manno C S, Pierce G F, Arruda V R, et al. Successful transduction of liver in hemophilia by AAV-Factor IX and limitations imposed by the host immune response. Nat Med. 2006; 12:342-347.
5. Mingozzi F, High K A. Immune responses to AAV in clinical trials. Curr Gene Ther. 2011; 11:321-330.
6. Mingozzi F, Maus M V, Hui D J, et al. CD8(+) T-cell responses to adeno-associated virus capsid in humans, Nat Med. 2007; 13:419-422.
7. Mingozzi F, Meulenberg J J, Hui D J, et al. AAV-1-mediated gene transfer to skeletal muscle in humans results in dose-dependent activation of capsid-specific T cells. Blood. 2009; 114:2077-2086.
8. Scallan C D, Jiang H, Liu T, et al. Human immunoglobulin inhibits liver transduction by AAV vectors at low AAV2 neutralizing titers in SCID mice. Blood. 2006; 107:1810-1817.
9. Jiang H, Couto L B, Patarroyo-White S, et al. Effects of transient immunosuppression on adenoassociated, virus-mediated, liver-directed gene transfer in rhesus macaques and implications for human gene therapy. Blood. 2006; 108:3321-3328.
10. Vincent N, Ragot T, Gilgenkrantz H, et al. Long-term correction of mouse dystrophic degeneration by adenovirus-mediated transfer of a minidystrophin gene. Nat Genet. 1993; 5:130-134.
11. Tinsley J M, Potter A C, Phelps S R, Fisher R, Trickett J I, Davies K E. Amelioration of the dystrophic phenotype of mdx mice using a truncated utrophin transgene. Nature. 1996; 384:349-353.
12. Finn J D, Hui D, Downey H D, et al. Proteasome inhibitors decrease AAV2 capsid derived peptide epitope presentation on MHC class I following transduction. Mol Ther. 2010; 18:135-142.
13. Pien G C, Basner-Tschakarjan E, Hui D J, et al. Capsid antigen presentation flags human hepatocytes for destruction after transduction by adeno-associated viral vectors. J Clin Invest. 2009; 119:1688-1695.
14. Tiwari M, Parida M, Santhosh S R, Khan M, Dash P K, Rao P V. Assessment of immunogenic potential of Vero adapted formalin inactivated vaccine derived from novel ECSA genotype of Chikungunya virus. Vaccine. 2009; 27:2513-2522.
15. Wright J F. Manufacturing and characterizing AAV-based vectors for use in clinical studies. Gene Ther. 2008; 15:840-848.
16. Sommer J M, Smith P H, Parthasarath S, et al. Quantification of adeno-associated virus particles and empty capsid by optical density measurement. Mol. Ther. 2003; 7:122-128.

What is claimed is:

1. A formulation comprising AAV vectors and AAV empty capsids, wherein said AAV vectors are in a 1:1 to 1:10,000 ratio to said AAV empty capsids said AAV vector comprising a transgene and wherein said AAV empty capsids bind to or react with antibodies present in a subject that would bind to or react with said AAV vector when administered to said subject and wherein said viral vector formulation comprises a surfactant and wherein said empty capsids are chemically modified to reduce or inhibit cellular uptake.

2. The formulation of claim 1, wherein said AAV vectors are in a 1:1 to 1:10,000 ratio to said AAV empty capsids.

3. The formulation of claim 1, wherein said viral AAV vectors are in a 1:1 to 1:50 ratio to said AAV empty capsids.

4. The formulation of claim 1, wherein said viral AAV vectors are in a 1:1 to 1:10 ratio to said AAV empty capsids.

5. A formulation comprising AAV vectors and AAV empty capsids, wherein said AAV vectors are in a 1:1 to 1:10,000 ratio to said AAV empty capsids said AAV vector comprising a transgene and wherein said AAV empty capsids bind to or react with antibodies present in a subject that would bind to or react with said AAV vector when administered to said subject and wherein said viral vector formulation comprises a surfactant and wherein said empty capsids are treated with a cross-linking agent, or comprise mutated capsids that exhibit reduced or decreased binding to AAV receptor expressed on cells.

6. The formulation of claim 5, wherein said mutated capsid comprises one or more arginine residues that contribute to heparan sulfate proteoglycan binding that has been substituted with a non-charged or hydrophobic residue.

7. The formulation of claim 6, wherein said mutated capsid comprises AAV2 with one or more arginine residues substituted at any of positions: 451, 448, 530, 585 or 588.

8. The formulation of claim 5, wherein said AAV vectors are in a 1:1 to 1:50 ratio to said AAV empty capsids.

9. The formulation of claim 5, wherein said AAV vectors are in a 1:1 to 1:10 ratio to said AAV empty capsids.

10. The formulation of claim 1 or 5, wherein said transgene sequence encodes a protein or peptide.

11. The formulation of claim 10, wherein said protein or peptide comprises a blood coagulation (clotting) factor.

12. The formulation of claim 11, wherein the blood coagulation (clotting) factor comprises Factor XIII, Factor IX, Factor X, Factor VIII, Factor VIIa, protein C, Factor VII, B domain-deleted Factor VIII, or a high-activity or longer half life variant of coagulation factor, or an active or inactive form of a coagulation factor.

13. The formulation of claim 11, wherein the blood coagulation (clotting) factor comprises Factor VIII.

14. The formulation of claim 1 or 5, wherein said transgene encodes a nucleic acid which upon expression modulates transcription of a genomic DNA, expression of a cognate mRNA, or stability or half-life of an RNA.

15. The formulation of claim 14, wherein said nucleic acid comprises an inhibitory polynucleotide.

16. The formulation of claim 1 or 5, wherein said AAV vectors are a serotype selected from the group consisting of AAV-1, -2, -3, -4, -5, -6, -7, -8, -9, -10, -11, -rh74, -rh10 and AAV-2i8, or comprise a capsid sequence at least 95% identical to an AAV-1, -2, -3, -4, -5, -6, -7, -8, -9, -10, -11, -rh74, -rh10 or AAV-2i8 vp1, vp2 and/or vp3 capsid sequence.

17. The formulation of claim 1 or 5, wherein said AAV empty capsids have reduced ability to transduce cells in vivo or in vitro compared to the AAV vectors, or wherein said AAV vectors have greater ability to transduce cells in vivo or in vitro compared to the AAV empty capsids.

18. The formulation of claim 17, wherein said cells comprise liver, pancreas, lung, central or peripheral nervous system cells, brain or spine cells, kidney, eye, spleen, skin, thymus, testes, lung, diaphragm, heart (cardiac), muscle or psoas, or gut cells, adipose tissue, muscle, synoviocytes, chondrocytes, osteoclasts, epithelial cells, endothelial cells, or salivary gland cells, inner ear nervous cells or hematopoietic cells; or stem cells, such as pluripotent or multipotent progenitor cells that develop or differentiate into liver cells, pancreas, lung, central or peripheral nervous system cells, brain or spine cells, kidney, eye, spleen, skin, thymus, testes, lung, diaphragm, heart (cardiac), muscle or psoas, or gut cells, adipose tissue, muscle, synoviocytes, chondrocytes, osteoclasts, epithelial cells, endothelial cells, or salivary gland cells, inner ear nervous cells, or hematopoietic cells.

19. The formulation of claim 1 or 5, wherein said AAV vectors and said AAV empty capsids (viral or said AAV vectors:AAV empty capsids) are in a ratio of about 1:1, 1:2, 1:3, 1:4, 1:5, 1:6, 1:7, 1:8, 1:9, 1:10, 1:11, 1:12, 1:13, 1:14, 1:15, 1:16, 1:18, 1:20, 1:21, 1:22, 1:23, 1:24, or 1:25.

20. A pharmaceutical composition comprising the formulation of claim 1 or 5 in a pharmaceutically acceptable carrier.

21. A method for delivering a transgene to a cell of a subject, comprising administration of an effective amount of the formulation of claim 1 or 5 to the subject in need thereof such that the transgene transduces the cell of the subject.

22. The method of claim 21, wherein said subject has a clotting disorder and said transgene encodes a clotting factor.

23. The method of claim 21, wherein said AAV vectors are a serotype selected from the group consisting of AAV-1, -2, -3, -4, -5, -6, -7, -8, -9, -10, -11, -rh74, -rh10 and AAV-2i8, or comprise a capsid sequence at least 95% identical to an AAV-1, -2, -3, -4, -5, -6, -7, -8, -9, -10, -11, -rh74, -rh10 or AAV-2i8 vp1, vp2, and/or vp3 capsid sequence.

24. The method of claim 21, wherein said AAV empty capsids are from an AAV serotype selected from the group consisting of AAV-1, -2, -3, -4, -5, -6, -7, -8, -9, -10, -11, -rh74, -rh10 and AAV-2i8, or comprise a capsid sequence at least 95% identical to an AAV-1, -2, -3, -4, -5, -6, -7, -8, -9, -10, -11, -rh74, -rh10 or AAV-2i8 vp1, vp2, and/or vp3 capsid sequence.

25. The method of claim 21, wherein said subject is human.

26. The method of claim 21, wherein said transgene sequence encodes a protein or peptide.

27. The method of claim 26, wherein said protein or peptide is selected from the group consisting of cystic fibrosis transmembrane regulator protein (CFTR), dystrophin, utrophin, blood coagulation (clotting) factor, a monoclonal antibody, retinal pigment epithelium-specific 65 kDa protein (RPE65), erythropoietin, LDL receptor, lipoprotein lipase, ornithine transcarbamylase, β-globin, α-globin, spectrin, α-antitrypsin, adenosine deaminase (ADA), a metal transporter (ATP7A or ATP7), sulfamidase, an enzyme involved in lysosomal storage disease (ARSA), hypoxanthine guanine phosphoribosyl transferase, β-25 glucocerebrosidase, sphingomyelinase, lysosomal hexosaminidase, branched-chain keto acid dehydrogenase, a hormone, a growth factor, insulin-like growth factor 1 or 2, platelet derived growth factor, epidermal growth factor, nerve growth factor, neurotrophic factor-3 and -4, brain-derived neurotrophic factor, glial derived growth factor, transforming growth factor α and β, a cytokine, α-interferon, β-interferon, interferon-γ, interleukin-2, interleukin-4, interleukin-12, granulocyte-macrophage colony stimulating factor, lymphotoxin, a suicide gene product, herpes simplex virus thymidine kinase, cytosine deaminase, diphtheria toxin, cytochrome P450, deoxycytidine kinase, tumor necrosis factor, a drug resistance protein, a tumor suppressor protein, VEGF, microdystrophin, lysosomal acid lipase, arylsulfatase A and B, ATP7A and B, a peptide with immunomodulatory properties, a tolerogenic or immunogenic peptide or protein Tregitope or hCDR1, insulin, glucokinase, guanylate cyclase 2D (LCA-GUCY2D), Rab escort protein 1 (Choroideremia), LCA 5 (LCA-Lebercilin), ornithine ketoacid aminotransferase (Gyrate Atrophy), Retinoschisin 1 (X-linked Retinoschisis), USH1C (Usher's Syndrome 1C), X-linked retinitis pigmentosa GTPase (XLRP), MERTK (AR forms of RP: retinitis pigmentosa), DFNB1 (Connexin 26 deafness), ACHM 2, 3 and 4 (Achromatopsia), PKD-1 or PKD-2 (Polycystic kidney disease), TPP1, CLN2, a gene product implicated in lysosomal storage diseases, cathepsin A, GM2-AP, NPC1, VPC2, a sphingolipid activator protein, or one or more zinc finger nucleases for genome editing, or donor sequences used as repair templates for genome editing.

28. The method of claim 21, wherein the subject is administered about $5 \times 10^{10}$ AAV vector genomes/kilogram (vg/kg) and/or about $4.5 \times 10^{11}$ AAV empty capsids/kilogram (cp/kg), for a total viral AAV vector/AAV empty capsid dose of about $5 \times 10^{11}$ vg+cp/kg.

* * * * *

SEQUENCE LISTING

```
<160> NUMBER OF SEQ ID NOS: 7

<210> SEQ ID NO 1
<211> LENGTH: 735
<212> TYPE: PRT
<213> ORGANISM: Adeno-associated virus

<400> SEQUENCE: 1

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60
```

-continued

Val Asn Glu Ala Asp Ala Ala Leu Glu His Asp Lys Ala Tyr Asp
65              70              75              80

Arg Gln Leu Asp Ser Gly Asp Asn Pro Tyr Leu Lys Tyr Asn His Ala
        85              90              95

Asp Ala Glu Phe Gln Glu Arg Leu Lys Glu Asp Thr Ser Phe Gly Gly
            100             105             110

Asn Leu Gly Arg Ala Val Phe Gln Ala Lys Lys Arg Val Leu Glu Pro
        115             120             125

Leu Gly Leu Val Glu Glu Pro Val Lys Thr Ala Pro Gly Lys Lys Arg
    130             135             140

Pro Val Glu His Ser Pro Val Glu Pro Asp Ser Ser Gly Thr Gly
145             150             155             160

Lys Ala Gly Gln Gln Pro Ala Arg Lys Arg Leu Asn Phe Gly Gln Thr
                165             170             175

Gly Asp Ala Asp Ser Val Pro Asp Pro Gln Pro Leu Gly Gln Pro Pro
            180             185             190

Ala Ala Pro Ser Gly Leu Gly Thr Asn Thr Met Ala Thr Gly Ser Gly
        195             200             205

Ala Pro Met Ala Asp Asn Asn Glu Gly Ala Asp Gly Val Gly Asn Ser
210             215             220

Ser Gly Asn Trp His Cys Asp Ser Thr Trp Met Gly Asp Arg Val Ile
225             230             235             240

Thr Thr Ser Thr Arg Thr Trp Ala Leu Pro Thr Tyr Asn Asn His Leu
                245             250             255

Tyr Lys Gln Ile Ser Ser Gln Ser Gly Ala Ser Asn Asp Asn His Tyr
            260             265             270

Phe Gly Tyr Ser Thr Pro Trp Gly Tyr Phe Asp Phe Asn Arg Phe His
        275             280             285

Cys His Phe Ser Pro Arg Asp Trp Gln Arg Leu Ile Asn Asn Asn Trp
    290             295             300

Gly Phe Arg Pro Lys Arg Leu Asn Phe Lys Leu Phe Asn Ile Gln Val
305             310             315             320

Lys Glu Val Thr Gln Asn Asp Gly Thr Thr Thr Ile Ala Asn Asn Leu
                325             330             335

Thr Ser Thr Val Gln Val Phe Thr Asp Ser Glu Tyr Gln Leu Pro Tyr
            340             345             350

Val Leu Gly Ser Ala His Gln Gly Cys Leu Pro Pro Phe Pro Ala Asp
        355             360             365

Val Phe Met Val Pro Gln Tyr Gly Tyr Leu Thr Leu Asn Asn Gly Ser
    370             375             380

Gln Ala Val Gly Arg Ser Ser Phe Tyr Cys Leu Glu Tyr Phe Pro Ser
385             390             395             400

Gln Met Leu Arg Thr Gly Asn Asn Phe Thr Phe Ser Tyr Thr Phe Glu
                405             410             415

Asp Val Pro Phe His Ser Ser Tyr Ala His Ser Gln Ser Leu Asp Arg
            420             425             430

Leu Met Asn Pro Leu Ile Asp Gln Tyr Leu Tyr Tyr Leu Ser Arg Thr
        435             440             445

Asn Thr Pro Ser Gly Thr Thr Thr Gln Ser Arg Leu Gln Phe Ser Gln
    450             455             460

Ala Gly Ala Ser Asp Ile Arg Asp Gln Ser Arg Asn Trp Leu Pro Gly
465             470             475             480

Pro Cys Tyr Arg Gln Gln Arg Val Ser Lys Thr Ser Ala Asp Asn Asn

```
            485                 490                 495
Asn Ser Glu Tyr Ser Trp Thr Gly Ala Thr Lys Tyr His Leu Asn Gly
        500                 505                 510

Arg Asp Ser Leu Val Asn Pro Gly Pro Ala Met Ala Ser His Lys Asp
    515                 520                 525

Asp Glu Glu Lys Phe Phe Pro Gln Ser Gly Val Leu Ile Phe Gly Lys
530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Forward
      primer

<400> SEQUENCE: 2
cgaattctag tcgtcgacca ct                                          22

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Reverse
      primer

<400> SEQUENCE: 3
catgttcacg cgctgcata                                              19

<210> SEQ ID NO 4
<211> LENGTH: 18
<212> TYPE: DNA
<213> ORGANISM: Artificial Sequence
<220> FEATURE:
```

```
<223> OTHER INFORMATION: Description of Artificial Sequence: Probe

<400> SEQUENCE: 4
cacaatctgc tagcaaag                                                 18

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Forward
      primer

<400> SEQUENCE: 5
aagctgaccc tgaagttcat c                                             21

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Reverse
      primer

<400> SEQUENCE: 6
ctgcttcatg tggtcggg                                                 18

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Probe
<220> FEATURE:
<221> NAME/KEY: misc_feature
<222> LOCATION: (11)..(11)
<223> OTHER INFORMATION: n is a, c, g, or t

<400> SEQUENCE: 7
aagcactgca ncgccgtagg ta                                            22
```